(12) United States Patent
Kadereit et al.

(10) Patent No.: US 8,735,402 B2
(45) Date of Patent: May 27, 2014

(54) CYCLOALKYLOXYCARBOXYLIC ACID DERIVATIVES

(75) Inventors: Dieter Kadereit, Frankfurt am Main (DE); Matthias Schaefer, Frankfurt am Main (DE); Stephanie Hachtel, Frankfurt am Main (DE); Thomas Huebschle, Frankfurt am Main (DE); Katrin Hiss, Frankfurt am Main (DE); Silke Haag-Diergarten, Frankfurt am Main (DE)

(73) Assignee: Sanofi, Paris (FR)

( * ) Notice: Subject to any disclaimer, the term of this patent is extended or adjusted under 35 U.S.C. 154(b) by 61 days.

(21) Appl. No.: 13/532,305

(22) Filed: Jun. 25, 2012

(65) Prior Publication Data

US 2013/0023545 A1     Jan. 24, 2013

(30) Foreign Application Priority Data

Jul. 7, 2011   (EP) .................................... 11305879
May 11, 2012   (EP) .................................... 12305527

(51) Int. Cl.

| A01N 43/90 | (2006.01) |
|---|---|
| A61K 31/519 | (2006.01) |
| C07D 471/00 | (2006.01) |
| C07D 487/00 | (2006.01) |
| C07D 491/00 | (2006.01) |

(52) U.S. Cl.
USPC ........................................ 514/260.1; 544/255

(58) Field of Classification Search
None
See application file for complete search history.

(56) References Cited

FOREIGN PATENT DOCUMENTS

| WO | 2009/154775 A1 | 12/2009 |
|---|---|---|
| WO | 2010/006704 A1 | 1/2010 |

*Primary Examiner* — Jeffrey H Murray
(74) *Attorney, Agent, or Firm* — Scully, Scott, Murphy & Presser, P.C.

(57) ABSTRACT

The present invention relates to cycloalkyloxycarboxylic acid derivatives of the formula I

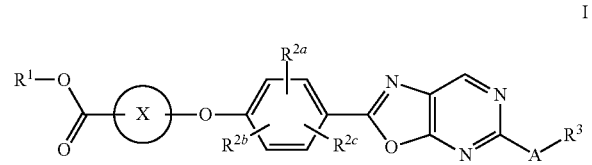

in which A, $R^1$, $R^{2a}$, $R^{2b}$, $R^{2c}$, $R^3$ and X are as defined in the claims. The compounds of the formula I are suitable, for example, for wound healing.

11 Claims, No Drawings

CYCLOALKYLOXYCARBOXYLIC ACID DERIVATIVES

The invention relates to cycloalkyloxycarboxylic acid derivatives, and to physiologically acceptable salts thereof.

Structurally similar compounds are already described in the prior art (see WO 2009/154775), which are suitable for treating multiple sclerosis. The mode of action of these compounds consists in causing a desensitization of the EDG 1 signal pathway by activating the EDG 1 receptor (so-called superagonism), which is then equivalent to a functional antagonism of the EDG 1 signal pathway. Systemically means that especially on lymphocytes, the EDG 1 signal pathway is permanently suppressed, as a result of which these cells can no longer chemotactically follow the S1P gradient between blood and lymph fluid. This means that the affected lymphocytes can no longer leave the secondary lymphatic tissue (increased homing) and the number of freely circulating lymphocytes in the plasma is greatly reduced. This deficiency of lymphocytes in the plasma (lymphopenia) brings about immunosuppression which is obligatorily required for the mechanism of action of the EDG 1 receptor modulators described in WO 2009/154775.

It was an object of the invention to provide compounds which display a therapeutically utilizable action. The object was in particular to find novel compounds which are suitable specifically for wound healing and in particular for the treatment of wound healing disorders in patients with diabetes. In addition, it was desirable to provide compounds which are suitable for the treatment of diabetic foot syndrome (DFS).

Furthermore, it was desirable to achieve a reproducible activation of the EDG 1 receptor signal pathway which thereby permits, in pharmacological terms, a persistent activation of the EDG 1 signal pathway.

The present invention relates to cycloalkyloxycarboxylic acid derivatives of the formula I

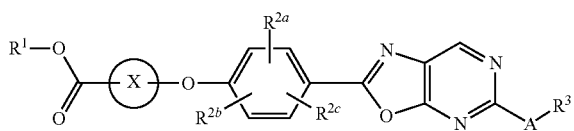

in which A, $R^1$, $R^{2a}$, $R^{2b}$, $R^{2c}$, $R^3$ and X are as defined below.

The mechanism of action of the compounds of the formula I is thus not based on desensitization of the EDG 1 signal pathway and is therefore in diametral opposition to the mechanism of action described in WO 2009/154775. The invention furthermore relates to processes for the preparation of compounds of the formula I, their use, in particular as active ingredients in pharmaceuticals, and pharmaceutical compositions comprising them.

Compared with healthy people, patients with diabetes have delayed wound healing and an increased rate of infection, especially in the case of long-term hyperglycemia, caused for example by poor blood sugar regulation. The causes include circulation disorders, especially in the area of the small vessels, which lead to impaired oxygen and nutrient supply of the tissue. Moreover, the cell division and cell migration rate of keratinocytes, fibroblasts and dermal endothelial cells is reduced. Additionally, the activity of various defense cells (granulocytes) with reduced phagocytosis (engulfing and destruction of bacteria) is restricted. The action of antibodies (immunoglobulins) against bacteria at high blood sugar levels is also restricted. Accordingly, wounds and infections in patients with diabetes have to be cared for in a particular way.

The Edg-1 receptor is a member of the endothelial differentiation gene (Edg) receptor family of currently eight identified class A GPCRs (G-protein coupled receptors). This family can be divided into subfamilies of sphingosine-1-phosphate (S1P)-activated receptors (five members) and receptors activated by lysophosphatidic acid (LPA; three members). The endogenous ligand S1P is a pluripotent lysophospholipid acting on different cell types by activating GPCRs from the Edg receptor family, namely Edg-1 (=S1P1), Edg-3 (=S1P3), Edg-5 (=S1P2), Edg-6 (=S1P4) and Edg-8 (S1P5). Although S1P is also described as an intracellular messenger, numerous cellular responses of S1P are mediated via the activation of Edg receptors. S1P is generated by the enzyme family of sphingosine kinases (SPHK) and degraded by different phosphatases or lyases.

Known indications of Edg-1 receptor agonists are, for example, cardiovascular disorders, atherosclerosis, heart failure, cardioprotection, peripheral arterial occlusive disease, kidney disorders and respiratory disorders.

The present invention provides compounds of the formula I in any of their stereoisomeric forms, or a mixture of stereoisomeric forms in any ratio, or a physiologically acceptable salt thereof, or a physiologically acceptable solvate of such a compound or such a salt,

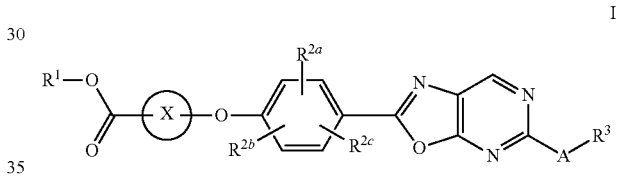

wherein
A is selected from the group consisting of NH, O and S;
X is $(C_3-C_7)$-cycloalkanediyl which is optionally substituted by one or more identical or different substituents selected from the group consisting of $(C_1-C_4)$-alkyl, fluorine and hydroxyl;
$R^1$ is selected from the group consisting of hydrogen, $(C_1-C_4)$-alkyl and $(C_3-C_7)$-cycloalkyl-$C_zH_{2z}$—, where z is selected from the group consisting of 0, 1 and 2;
$R^{2a}$, $R^{2b}$, and $R^{2c}$ are selected independently of one another from the group consisting of hydrogen, halogen, hydroxyl, $(C_1-C_4)$-alkyl-, $(C_3-C_5)$-cycloalkyl-$C_zH_{2z}$—, $(C_1-C_4)$-alkyloxy, $(C_1-C_4)$-alkyl-$S(O)_m$—, amino, nitro, cyano, hydroxycarbonyl, $(C_1-C_4)$-alkyloxycarbonyl, aminocarbonyl and aminosulfonyl, where z is selected from the group consisting of 0, 1 and 2;
$R^3$ is selected from the group consisting of $(C_1-C_6)$-alkyl, $(C_2-C_6)$-alkenyl, $(C_2-C_6)$-alkynyl, $(C_3-C_7)$-cycloalkyl-$C_uH_{2u}$— or Het-$C_vH_{2v}$—, where u and v are selected from the group consisting of 1 and 2, or $R^3$ is a radical of a saturated or unsaturated 3-membered to 10-membered monocyclic or bicyclic ring which contains 0, 1, 2, 3 or 4 identical or different ring heteroatoms selected from the group consisting of N, O and S, where one or two of the ring nitrogen atoms may carry a hydrogen atom or a $(C_1-C_4)$-alkyl substituent and one or two of the ring sulfur atoms may carry one or two oxo groups and where the radical of a ring is optionally substituted at one or more ring carbon atoms by identical or different substituents $R^{31}$;
$R^{31}$ is selected from the group consisting of halogen, $(C_1-C_4)$-alkyl, $(C_3-C_7)$-cycloalkyl, hydroxyl, $(C_1-C_4)$-alkyloxy, oxo, $(C_1-C_4)$-alkyl-S(O)$_m$—, amino, $(C_1-C_4)$-alkylamino, di($(C_1-C_4)$-alkyl)amino, $(C_1-C_4)$-alkylcarbonylamino, $(C_1-C_4)$-alkylsulfonylamino, nitro, cyano, $(C_1-C_4)$-alkylcarbonyl, aminosulfonyl, $(C_1-C_4)$-alkylaminosulfonyl and di($(C_1-C_4)$-alkyl)aminosulfonyl;

Het is a radical of a saturated 4-membered to 7-membered monocyclic heterocycle which contains 1 or 2 identical or different ring heteroatoms selected from the group consisting of N, O and S and which is attached via a ring carbon atom, where the radical of a heterocycle is optionally substituted by one or more identical or different substituents selected from the group consisting of fluorine and $(C_1-C_4)$-alkyl;

m is selected from the group consisting of 0, 1 and 2;

where all cycloalkyl and cycloalkanediyl groups independently of one another and independently of other substituents are optionally substituted by one or more identical or different substituents selected from the group consisting of fluorine and $(C_1-C_4)$-alkyl;

where all alkyl, alkanediyl, $C_uH_{2u}$, $C_vH_{2v}$, $C_zH_{2z}$, alkenyl, alkenediyl, alkynyl and alkynediyl groups independently of one another and independently of other substituents may optionally be substituted by one or more fluorine substituents.

Structural elements such as groups, substituents, hetero ring members, numbers or other features, for example alkyl groups, groups like $R^{22}$ or $R^{31}$, numbers like m, u and v, which can occur several times in the compounds of the formula I, can all independently of one another have any of the indicated meanings and can in each case be identical to or different from one another. For example, the alkyl groups in a dialkylamino group can be identical or different.

Alkyl, alkenyl and alkynyl groups can be linear, i.e. straight-chain, or branched. This also applies when they are part of other groups, for example alkyloxy groups (=alkoxy groups, alkyl O groups), alkyloxycarbonyl groups or alkyl-substituted amino groups, or when they are substituted. Depending on the respective definition, the number of carbon atoms in an alkyl group can be 1, 2, 3, 4, 5 or 6, or 1, 2, 3 or 4, or 1, 2 or 3. Examples of alkyl are methyl, ethyl, propyl including n-propyl and isopropyl, butyl including n-butyl, sec-butyl, isobutyl and tert-butyl, pentyl including n-pentyl, 1-methylbutyl, isopentyl, neopentyl and tert-pentyl, and hexyl including n-hexyl, 3,3-dimethylbutyl and isohexyl. Double bonds and triple bonds in alkenyl groups and alkynyl groups can be present in any positions. In one embodiment of the invention, alkenyl groups contain one double bond and alkynyl groups contain one triple bond. In one embodiment of the invention, an alkenyl group or alkynyl group contains at least three carbon atoms and is bonded to the remainder of the molecule via a carbon atom which is not part of a double bond or triple bond. Examples of alkenyl and alkynyl are ethenyl, prop-1-enyl, prop-2-enyl (=allyl), but-2-enyl, 2-methylprop-2-enyl, 3-methylbut-2-enyl, hex-3-enyl, hex-4-enyl, prop-2-ynyl (=propargyl), but-2-ynyl, but-3-ynyl, hex-4-ynyl or hex-5-ynyl. Substituted alkyl groups, alkenyl groups and alkynyl groups can be substituted in any positions, provided that the respective compound is sufficiently stable and is suitable for the desired purpose, such as use as a drug substance. The prerequisite that a specific group and a compound of the formula I are sufficiently stable and suitable for the desired purpose, such as use as a drug substance, applies in general with respect to the definitions of all groups in the compounds of the formula I.

As far as applicable, the preceding explanations regarding alkyl, alkenyl and alkynyl groups apply correspondingly to divalent alkyl groups such as the groups alkanediyl $C_uH_{2u}$, $C_vH_{2v}$, $C_wH_{2w}$, and $C_zH_{2z}$ and bivalent alkenyl groups and alkynyl groups, such as the groups alkenediyl and alkyndiyl, which thus can likewise be linear and branched. The double bonds and triple bonds in alkenediyl and alkynediyl groups can be present in any positions. In one embodiment of the invention, alkenediyl groups contain one double bond and alkynediyl groups contain one triple bond. Examples of divalent alkyl groups are —CH$_2$— (=methylene), —CH$_2$—CH$_2$—, —CH$_2$—CH$_2$—CH$_2$—, —CH$_2$—CH$_2$—CH$_2$—CH$_2$—, —CH(CH$_3$)—, —C(CH$_3$)$_2$—, —CH(CH$_3$)—CH$_2$—, —CH$_2$—CH(CH$_3$)—, —C(CH$_3$)$_2$—CH$_2$—, —CH$_2$—C(CH$_3$)$_2$—, examples of divalent alkenyl groups are —CH=CH—, —CH$_2$—CH=CH—, —CH=CH—CH$_2$—, —CH$_2$—CH=CH—CH$_2$—, —CH$_2$—CH$_2$—CH=CH—, —C(CH$_3$)=C(CH$_3$)—, and examples of divalent alkynyl groups are —C≡C—, —CH$_2$—C≡C—, —C≡C—CH$_2$—, —C(CH$_3$)$_2$—C≡C—, —C≡C—C(CH$_3$)$_2$—, —CH$_2$—C≡C—CH$_2$—, —CH$_2$—CH$_2$—C≡C—. If a number in a divalent group such as the number z in the group $C_zH_{2z}$, for example, is 0 (=zero), the two groups which are attached to the contemplated group, such as $C_zH_{2z}$, are directly connected to one another via a single bond.

The number of ring carbon atoms in a cycloalkyl group can be 3, 4, 5, 6 or 7. In one embodiment of the invention, the number of ring carbon atoms in a cycloalkyl group, independently of the number of ring carbon atoms in any other cycloalkyl group, is 3, 4, 5 or 6, in another embodiment 3, 4 or 5, in another embodiment 3 or 4, in another embodiment 3, in another embodiment 5, 6 or 7, in another embodiment 5 or 6, in another embodiment 6 or 7, in another embodiment 6. This applies accordingly to divalent cycloalkyl groups, i.e. cycloalkanediyl groups, which can be bonded to the adjacent groups via any one or two ring carbon atoms. Examples of cycloalkyl groups are cyclopropyl, cyclobutyl, cyclopentyl, cyclohexyl and cycloheptyl. Examples of divalent cycloalkyl groups are cyclopropane-1,1-diyl, cyclopropane-1,2-diyl, cyclobutane-1,3-diyl, cyclopentane-1,1-diyl, cyclopentane-1,2-diyl, cyclopentane-1,3-diyl, cyclohexane-1,1-diyl, cyclohexane-1,2-diyl, cyclohexane-1,3-diyl, cyclohexane-1,4-diyl, cycloheptane-1,4-diyl. Independently of one another and independently of any other substituents, cycloalkyl groups and cycloalkanediyl groups are optionally substituted by one or more identical or different $(C_1-C_4)$-alkyl substituents which can be located in any positions, i.e., cycloalkyl groups can be unsubstituted by alkyl substituents or substituted by alkyl substituents, for example by 1, 2, 3 or 4, or by 1 or 2, $(C_1-C_4)$-alkyl substituents, for example by methyl groups. Examples of alkyl-substituted cycloalkyl groups and cycloalkanediyl groups are 4-methylcyclohexyl, 4-tert-butyl-cyclohexyl or 2,3-dimethylcyclopentyl, 2,2-dimethylcyclopropane-1,1-diyl, 2,2-dimethylcyclopropane-1,2-diyl, 2,2-dimethylcyclopentane-1,3-diyl, 6,6-dimethylcycloheptane-1,4-diyl. Examples of cycloalkylalkyl groups, which can represent groups such as $(C_3-C_7)$-cycloalkyl-$C_zH_{2z}$—, for example, are cyclopropylmethyl, cyclobutylmethyl, cyclopentylmethyl, cyclohexylmethyl, cycloheptylmethyl, 1-cyclopropylethyl, 2-cyclopropylethyl, 1-cyclobutylethyl, 2-cyclobutylethyl, 2-cyclopentylethyl, 2-cyclohexylethyl, 2-cycloheptylethyl.

Independently of one another and independently of any other substituents, alkyl groups, divalent alkyl groups, alkenyl groups, divalent alkenyl groups, alkynyl groups, divalent alkynyl groups, cycloalkyl groups and divalent cycloalkyl groups are optionally substituted by one or more fluorine substituents which can be located in any positions, i.e., said groups can be unsubstituted by fluorine substituents or substituted by fluorine substituents, for example by 1, 2, 3, 4, 5, 6, 7, 8, 9, 10, 11, 12 or 13, or by 1, 2, 3, 4, 5, 6, 7, 8 or 9, or by 1, 2, 3, 4, 5, 6 or 7, or by 1, 2, 3, 4 or 5, or by 1, 2 or 3, or by 1 or 2, fluorine substituents. Examples of such fluorine-substituted groups are trifluoromethyl, 2-fluoroethyl, 2,2,2-trifluoroethyl, pentafluoroethyl, 3,3,3-trifluoropropyl, 2,2,3,3,3-pentafluoropropyl, 4,4,4-trifluorobutyl, heptafluoroisopropyl, —CHF—, —CF$_2$—, —CF$_2$—CH$_2$—, —CH$_2$—CF$_2$—, —CF$_2$—CF$_2$—, —CF(CH$_3$)—, —C(CF$_3$)$_2$—, 1-fluorocyclopropyl, 2,2-difluorocyclopropyl, 3,3-difluorocyclobutyl, 1-fluorocyclohexyl, 4,4-difluorocyclohexyl, 3,3,4,4,5,5-hexafluorocyclohexyl, 2,2-difluorocyclopropane-1,2-diyl. Examples of alkyloxy groups in which the alkyl moiety is fluorine-substituted are trifluoromethoxy, 2,2,2-trifluoroethoxy, pentafluoroethoxy and 3,3,3-trifluoropropoxy. In one embodiment of the invention, the total number of fluorine substituents and (C$_1$-C$_4$)-alkyl substituents, which independently of any other substituents are optionally present on cycloalkyl groups and cycloalkanediyl groups in the compounds of the formula I, is 1, 2, 3, 4, 5, 6, 7, 8, 9, 10 or 11, in another embodiment 1, 2, 3, 4, 5, 6, 7, 8 or 9, in another embodiment 1, 2, 3, 4 or 5, in another embodiment 1, 2, 3 or 4.

Groups like phenyl, naphthyl (=naphthalenyl) and residues of aromatic heterocycles which are optionally substituted by one or more substituents can be unsubstituted or substituted, for example by 1, 2, 3, 4 or 5, or by 1, 2, 3 or 4, or by 1, 2 or 3, or by 1 or 2, or by 1, identical or different substituents which can be located in any positions. In one embodiment of the invention the total number of nitro substituents in a compound of the formula I is not greater than two. Aromatic nitrogen heterocycles which in the parent ring system carry a hydrogen atom on a ring nitrogen atom in a 5-membered ring, such as a pyrrole, imidazole, indole or benzimidazole ring, for example, can be substituted on the carbon atoms and/or on such ring nitrogen atoms. In one embodiment of the invention, substituents on such ring nitrogen atoms are chosen from (C$_1$-C$_4$)-alkyl groups, i.e. such ring nitrogen atoms in aromatic heterocycles carry a hydrogen atom or a (C$_1$-C$_4$)-alkyl substituent. When it is stated with respect to ring nitrogen atoms in aromatic heterocycles and any other heterocycles that they can carry a hydrogen atom or a substituent, such ring nitrogen atoms either carry a hydrogen atom or a substituent, or they do not carry a hydrogen atom or substituent. Ring nitrogen atoms which carry a hydrogen atom or a substituent occur in a nitrogen-containing aromatic 5-membered ring as is present in pyrrole, imidazole, indole or benzimidazole, for example, and in a non-aromatic ring including a saturated ring. Ring nitrogen atoms which do not carry a hydrogen atom or a substituent unless they are present in positively charged form, including any further ring nitrogen atoms in addition to ring nitrogen atoms which carry a hydrogen atom or a substituent, occur in an aromatic ring as is present in thiazole, imidazole, pyridine or benzimidazole, for example, and in a non-aromatic ring in which they are bridgehead atoms or are part of a double bond, and they occur as ring nitrogen atoms via which a ring is bonded. Suitable ring nitrogen atoms in aromatic heterocycles in the compounds of the formula I, such as the ring nitrogen atom in a pyridine ring, specifically a ring nitrogen atom in an aromatic heterocycle representing R$^2$, can also carry an oxy substituent —O$^-$ and be present as an N-oxide, and such ring nitrogen atoms can also be present as quaternary salt, for example as N—(C$_1$-C$_4$)-alkyl salt such as N-methyl salt, wherein in one embodiment of the invention the counter anion in such a quaternary salt is a physiologically acceptable anion which is derived from an acid that forms a physiologically acceptable salt. In monosubstituted phenyl groups, the substituent can be located in the 2-position, the 3-position or the 4-position. In disubstituted phenyl groups, the substituents can be located in 2,3-position, 2,4-position, 2,5-position, 2,6-position, 3,4-position or 3,5-position. In trisubstituted phenyl groups, the substituents can be located in 2,3,4-position, 2,3,5-position, 2,3,6-position, 2,4,5-position, 2,4,6-position or 3,4,5-position. Naphthyl can be 1-naphthyl (=naphthalen-1-yl) or 2-naphthyl (=naphthalen-2-yl). In monosubstituted 1-naphthyl groups, the substituent can be located in the 2-, 3-, 4-, 5-, 6-, 7- or 8-position. In monosubstituted 2-naphthyl groups, the substituent can be located in the 1-, 3-, 4-, 5-, 6-, 7- or 8-position. In disubstituted naphthyl groups, the substituents can likewise be located in any positions both in the ring via which the naphthyl group is bonded and/or in the other ring. This statement relating to the monovalent residues applies accordingly to the respective divalent residues, such as phenylene groups representing R$^2$, for example, which thus can likewise be unsubstituted or substituted, for example by 1, 2, 3 or 4, or by 1, 2 or 3, or by 1 or 2, or by 1, identical or different substituents which can be located in any positions.

In radicals of aromatic heterocycles representing R$^3$, which may be designated as heteroaryl and heteroarylene groups, as well as in all other heterocyclic rings in the compounds of the formula I including the group Het and the non-aromatic heterocyclic groups representing R$^3$, the ring heteroatoms are generally selected from the group consisting of N, O and S, where N includes ring nitrogen atoms which carry a hydrogen atom or a substituent as well as ring nitrogen atoms which do not carry a hydrogen atom or a substituent. Ring heteroatoms can be located in any positions, provided that the heterocyclic system is known in the art and is stable and suitable as a subgroup for the desired purpose of the compound of the formula I such as use as a drug substance. In one embodiment of the invention, two ring oxygen atoms cannot be present in adjacent ring positions of any heterocycle, in another embodiment two ring heteroatoms chosen from oxygen and sulfur cannot be present in adjacent ring positions of any heterocycle. Saturated rings do not contain a double bond within the ring. Unsaturated ring systems can be aromatic or partially unsaturated including partially aromatic, in which latter case one ring in a bicyclic ring system is aromatic and the ring system is bonded via an atom in the non-aromatic ring. Depending on the respective group, unsaturated rings can contain one, two, three, four or five double bonds within the ring. Aromatic groups contain a cyclic system of six or ten delocalized pi electrons in the ring. Depending on the respective group, saturated and non-aromatic unsaturated heterocyclic rings, including Het and non-aromatic groups representing R$^3$, can be 3-membered, 4-membered, 5-membered, 6-membered, 7-membered, 8-membered, 9-membered or 10-membered. In one embodiment of the invention, aromatic heterocyclic rings are 5-membered or 6-membered monocyclic rings or 8-membered, 9-membered or 10-membered bicyclic rings, in another embodiment 5-membered or 6-membered monocyclic rings or 9-membered or 10-membered bicyclic rings, in another embodiment 5-membered or 6-membered monocyclic rings, wherein the 8-membered, 9-membered or 10-membered bicyclic rings are composed of two fused 5-membered rings, a 5-membered ring and a 6-membered ring which are fused to one another, and two fused 6-membered rings, respectively. In bicyclic aromatic heterocyclic groups, one or both rings can contain hetero ring members, and one or both rings can be aromatic. In general, bicyclic ring systems containing an aromatic ring and a non-aromatic ring are regarded as aromatic when they are bonded via a carbon atom in the aromatic ring, and as non-aromatic when they are bonded via a carbon atom in the non-aromatic ring. Unless stated otherwise, heterocyclic groups including aromatic heterocyclic groups can be bonded via any suitable ring carbon atom and, in the case of nitrogen heterocycles, via any suitable ring nitrogen atom. In one embodiment of the invention, an aromatic heterocyclic group in a compound of the formula I, independently of any other aromatic heterocyclic group, is bonded via a ring carbon atom, in another embodiment via a ring nitrogen atom. Depending on the definition of the respective heterocyclic group, in one embodiment of the invention the number of ring heteroatoms which can be present in a heterocyclic group, independently of the number of ring heteroatoms in any other heterocyclic group, is 1, 2, 3 or 4, in another embodiment 1, 2 or 3, in another embodiment 1 or 2, in another embodiment 1, wherein the ring heteroatoms can be identical or different. Heterocyclic groups which are optionally substituted, can independently of any other heterocyclic group be unsubstituted or substituted by one or more identical or different substituents, for example by 1, 2, 3, 4 or 5, or by 1, 2, 3 or 4, or by 1, 2 or 3, or by 1 or 2, or by 1 substituents, which are indicated in the definition of the respective group. Substituents on heterocyclic groups can be located in any positions. For example, in a pyridin-2-yl group substituents can be located in the 3-position and/or 4-position and/or 5-position and/or 6-position, in a pyridin-3-yl group substituents can be located in the 2-position and/or 4-position and/or 5-position and/or 6-position, and in a pyridin-4-yl group substituents can be located in the 2-position and/or 3-position and/or 5-position and/or 6-position.

Examples of parent heterocycles, from which heterocyclic groups including aromatic heterocyclic groups, saturated heterocyclic groups and non-aromatic unsaturated heterocyclic groups can be derived, are azete, oxete, pyrrole, furan, thiophene, imidazole, pyrazole, [1,3]dioxole, oxazole (=[1,3]oxazole), isoxazole (=[1,2]oxazole), thiazole (=[1,3]thiazole), isothiazole (=[1,2]thiazole), [1,2,3]triazole, [1,2,4]triazole, [1,2,4]oxadiazole, [1,3,4]oxadiazole, [1,2,4]thiadiazole, [1,3,4]thiadiazole, tetrazole, pyridine, pyran, thiopyran, pyridazine, pyrimidine, pyrazine, [1,3]oxazine, [1,4]oxazine, [1,3]thiazine, [1,4]thiazine, [1,2,3]triazine, [1,3]dithiine, [1,4]dithiine, [1,2,4]triazine, [1,3,5]triazine, [1,2,4,5]tetrazine, azepine, [1,3]diazepine, [1,4]diazepine, [1,3]oxazepine, [1,4]oxazepine, [1,3]thiazepine, [1,4]thiazepine, azocine, azecine, cyclopenta[b]pyrrole, 2-azabicyclo[3.1.0]hexane, 3-azabicyclo[3.1.0]hexane, 2-oxa-5-azabicyclo[2.2.1]heptane, indole, isoindole, benzothiophene, benzofuran, [1,3]benzodioxole (=1,2-methylenedioxybenzene), [1,3]benzoxazole, [1,3]benzothiazole, benzoimidazole, thieno[3,2-c]pyridine, chromene, isochromene, [1,4]benzodioxine, [1,4]benzoxazine, [1,4]benzothiazine, quinoline, isoquinoline, cinnoline, quinazoline, quinoxaline, phthalazine, thienothiophene, [1,8]naphthyridine and other naphthyridines, pteridine, and the respective saturated and partially saturated heterocycles in which one or more, for example one, two, three, four or all double bonds within the ring system including the double bonds in the aromatic ring are replaced with single bonds, such as azetidine, oxetane, pyrrolidine, tetrahydrofuran, tetrahydrothiophene, imidazolidine, oxazolidine, thiazolidine, dihydropyridine, piperidine, tetrahydropyran, piperazine, morpholine, thiomorpholine, azepane, chroman, isochroman, [1,4]benzodioxane (=1,2-ethylenedioxybenzene), 2,3-dihydrobenzofuran, 1,2,3,4-tetrahydroquinoline, 1,2,3,4-tetrahydroisoquinoline, for example.

Examples of residues of aromatic heterocycles, which can occur in the compounds of the formula I, are thiophenyl (=thienyl) including thiophen-2-yl and thiophen-3-yl, pyridinyl (=pyridyl) including pyridin-2-yl (=2-pyridyl), pyridin-3-yl (=3-pyridyl) and pyridin-4-yl (=4-pyridyl), imidazolyl including, for example, 1H-imidazol-1-yl, 1H-imidazol-2-yl, 1H-imidazol-4-yl and 1H-imidazol-5-yl, [1,2,4]triazolyl including 1H-[1,2,4]-triazol-1-yl and 4H-[1,2,4]-triazol-3-yl, tetrazolyl including 1H-tetrazol-1-yl and 1H-tetrazol-5-yl, quinolinyl (=quinolyl) including quinolin-2-yl, quinolin-3-yl, quinolin-4-yl, quinolin-5-yl, quinolin-6-yl, quinolin-7-yl and quinolin-8-yl, which all are optionally substituted as indicated in the definition of the respective group. Examples of residues of saturated and partially unsaturated heterocycles, which can occur in the compounds of the formula I, are azetidinyl, pyrrolidinyl including pyrrolidin-1-yl, pyrrolidin-2-yl and pyrrolidin-3-yl, 2,5-dihydro-1H-pyrrolyl, piperidinyl including piperidin-1-yl, piperidin-2-yl, piperidin-3-yl and piperidin-4-yl, 1,2,3,4-tetrahydropyridinyl, 1,2,5,6-tetrahydropyridinyl, 1,2-dihydropyridinyl, azepanyl, azocanyl, azecanyl, octahydrocyclopenta[b]pyrrolyl, 2,3-dihydrobenzofuranyl including 2,3-dihydrobenzofuran-7-yl, 2,3-dihydro-1H-indolyl, octahydro-1H-indolyl, 2,3-dihydro-1H-isoindolyl, octahydro-1H-isoindolyl, 1,2-dihydroquinolinyl, 1,2,3,4-tetrahydroquinolinyl, decahydroquinolinyl, 1,2-dihydroisoquinolinyl, 1,2,3,4-tetrahydroisoquinolinyl, 1,2,3,4-tetrahydroisoquinolinyl, decahydroisoquinolinyl, decahydroisoquinolinyl, 4,5,6,7-tetrahydrothieno[3,2-c]pyridinyl, pyrazolidinyl, imidazolidinyl, hexahydropyrimidinyl, 1,2-dihydropyrimidinyl, piperazinyl, [1,3]diazepanyl, [1,4]diazepanyl, oxazolidinyl, [1,3]oxazinanyl, [1,3]oxazepanyl, morpholinyl including morpholin-2-yl, morpholin-3-yl and morpholin-4-yl, [1,4]oxazepanyl, thiazolidinyl, [1,3]thiazinanyl, thiomorpholinyl including thiomorpholin-2-yl, thiomorpholin-3-yl and thiomorpholin-4-yl, 3,4-dihydro-2H-[1,4]thiazinyl, [1,3]thiazepanyl, [1,4]thiazepanyl, oxetanyl, tetrahydrofuranyl, tetrahydrothienyl, isoxazolidinyl, isothiazolidinyl, oxazolidinyl, [1,2,4]-oxadiazolidinyl, [1,2,4]-thiadiazolidinyl, [1,2,4]triazolidinyl, [1,3,4]oxadiazolidinyl, [1,3,4]thiadiazolidinyl, [1,3,4]triazolidinyl, 2,3-dihydrofuranyl, 2,5-dihydrofuranyl, 2,3-dihydrothienyl, 2,5-dihydrothienyl, 2,3-dihydropyrrolyl, 2,3-dihydroisoxazolyl, 4,5-dihydroisoxazolyl, 2,5-dihydroisoxazolyl, 2,3-dihydroisothiazolyl, 4,5-dihydroisothiazolyl, 2,5-dihydroisothiazolyl, 2,3-dihydropyrazolyl, 4,5-dihydropyrazolyl, 2,5-dihydropyrazolyl, 2,3-dihydrooxazolyl, 4,5-dihydrooxazolyl, 2,5-dihydrooxazolyl, 2,3-dihydrothiazolyl, 4,5-dihydrothiazolyl, 2,5-dihydrothiazolyl, 2,3-dihydroimidazolyl, 4,5-dihydroimidazolyl, 2,5-dihydroimidazolyl, 2,5-dihydropyridazinyl, tetrahydropyrimidinyl, tetrahydropyrazinyl, tetrahydro[1,3,5]triazinyl, [1,3]dithianyl, tetrahydropyranyl, tetrahydrothiopyranyl, [1,3]dioxolanyl, 3,4,5,6-tetrahydropyridinyl, 4H-[1,3]thiazinyl, 1,1-dioxo-2,3,4,5-tetrahydrothienyl, 2-azabicyclo[3.1.0]hexyl including 2-azabicyclo[3.1.0]hex-2-yl, 3-azabicyclo[3.1.0]hexyl including 3-azabicyclo[3.1.0]hex-3-yl, 2-oxa-5-azabicyclo[2.2.1]heptyl including 2-oxa-5-azabicyclo[2.2.1]hept-5-yl, which all are bonded via any suitable ring carbon atom or ring nitrogen atom and are optionally substituted as indicated in the definition of the respective group.

Halogen is fluorine, chlorine, bromine or iodine. In one embodiment of the invention, any halogen in a compound of the formula I is independently of any other halogen chosen from fluorine, chlorine and bromine, in another embodiment from fluorine and chlorine.

When an oxo group is bonded to a carbon atom, it replaces two hydrogen atoms on a carbon atom of the parent system. Thus, if a $CH_2$ group in a chain or a ring is substituted by oxo, i.e. by a doubly bonded oxygen atom, it becomes a C(O) (=C(=O)) group. Evidently, an oxo group cannot occur as a substituent on a carbon atom in an aromatic ring such as in a phenyl group, for example. When a ring sulfur atom in a heterocyclic group can carry one or two oxo groups, it is a non-oxidized sulfur atom S in the case that it does not carry any oxo group, or it is an S(O) group (sulfoxide group, S oxide group) in the case that it carries one oxo group, or it is an $S(O)_2$ group (=sulfone group, S,S dioxide group) in the case that it carries two oxo groups.

The present invention includes all stereoisomeric forms of the compounds of the formula I and their salts and solvates. With respect to each chiral center, independently of any other chiral center, the compounds of the formula I can be present in S configuration or substantially S configuration, or in R configuration or substantially R configuration, or as a mixture of the S isomer and the R isomer in any ratio. The invention includes all possible enantiomers and diastereomers and mixtures of two or more stereoisomers, for example mixtures of enantiomers and/or diastereomers, in all ratios. Thus, compounds according to the invention which can exist as enantiomers can be present in enantiomerically pure form, both as levorotatory and as dextrorotatory antipodes, and in the form of mixtures of the two enantiomers in all ratios including racemates. In the case of an E/Z isomerism, or cis/trans isomerism, for example on double bonds or rings such as cycloalkyl rings, the invention includes both the E form and Z form, or the cis form and the trans form, as well as mixtures of these forms in all ratios. In one embodiment of the invention, a compound which can occur in two or more stereoisomeric forms is a pure, or substantially pure, individual stereoisomer. The preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally, a derivatization can be carried out before a separation of stereoisomers. The separation of a mixture of stereoisomers can be carried out at the stage of the compound of the formula I or at the stage of a starting material or an intermediate during the synthesis. The present invention also includes all tautomeric forms of the compounds of the formula I and their salts and solvates.

In case the compounds of the formula I contain one or more acidic and/or basic groups, i.e. salt-forming groups, the invention also includes their corresponding physiologically or toxicologically acceptable salts, i.e. non-toxic salts, in particular their pharmaceutically acceptable salts.

The present invention includes all solvates of compounds of the formula I, for example hydrates or adducts with alcohols such as $(C_1-C_4)$-alkanols, active metabolites of the compounds of the formula I, and also prodrugs and derivatives of the compounds of the formula I which in vitro may not necessarily exhibit pharmacological activity but which in vivo are converted into pharmacologically active compounds, for example esters or amides of carboxylic acid groups.

In one embodiment of the invention, A is selected from the group consisting of NH and O, in another embodiment A is selected from the group consisting of NH and S, in another embodiment A is selected from the group consisting of O and S, in another embodiment A is NH, in another embodiment A is O, in another embodiment A is S.

In the case of the cycloalkanediyl group representing X, in one embodiment the groups $R^1O$—$C(O)$ and the phenyl ring are bonded to two ring carbon atoms which are in 1,2-position, 1,3-position or 1,4-position with respect to each other, in another embodiment in 1,2-position or 1,3-position with respect to each other, in another embodiment in 1,2-position with respect to each other, in another embodiment in 1,4-position with respect to each other. In one embodiment, the $(C_3-C_7)$-cycloalkanediyl group which represents X is a $(C_3-C_6)$-cycloalkanediyl group, in another embodiment a $(C_3-C_4)$-cycloalkanediyl group, in another embodiment a cyclopropanediyl group, in another embodiment a cyclobutanediyl group, in another embodiment a cyclopentanediyl group, in another embodiment a cyclohexanediyl group, where all these groups may be substituted as specified. In one embodiment, the number of substituents which are optionally present in X is 0, 1, 2, 3 or 4, in another embodiment 0, 1, 2 or 3, in another embodiment 0, 1 or 2, in another embodiment 0 or 1, in another embodiment 1, and in another embodiment the group X is not substituted by substituents selected from the group consisting of $(C_1-C_4)$-alkyl, fluorine and hydroxyl. In one embodiment, the number of hydroxy substituents in X is not greater than 2, in another embodiment not greater than 1. In one embodiment, no more than one hydroxy substituent is present on an individual carbon atom in X.

In one embodiment of the invention, the number z is chosen from 0 and 1, in another embodiment it is 0, in another embodiment it is 1. In one embodiment of the invention, the group $R^1$ is selected from the group consisting of hydrogen and $(C_1-C_4)$-alkyl, in another embodiment $R^1$ is selected from hydrogen, methyl, ethyl, n-propyl, n-butyl and isopropyl, in another embodiment from hydrogen, methyl and ethyl, in another embodiment $R^1$ is hydrogen, in another embodiment $R^1$ is $(C_1-C_4)$-alkyl, in another embodiment $R^1$ is methyl and in another embodiment $R^1$ is ethyl. In one embodiment, a $(C_3-C_7)$-cycloalkyl group which is present in $R^1$ is $(C_3-C_6)$-cycloalkyl, in another embodiment it is cyclopropyl.

In one embodiment of the invention, the substituents $R^{2a}$, $R^{2b}$ and $R^{2c}$ independently of one another are selected from the group consisting of hydrogen, halogen, hydroxyl, $(C_1-C_4)$-alkyl-, $(C_1-C_4)$-alkyloxy-, $(C_1-C_4)$-alkyl-$S(O)_m$—, amino, nitro and cyano, in another embodiment from hydrogen, halogen, hydroxyl, $(C_1-C_4)$-alkyl-, $(C_1-C_4)$-alkyloxy-, amino and cyano, in another embodiment from hydrogen, halogen, hydroxyl, $(C_1-C_4)$-alkyl- and $(C_1-C_4)$-alkyloxy-, in another embodiment from hydrogen, fluorine, chlorine, hydroxyl, $(C_1-C_4)$-alkyl- and $(C_1-C_4)$-alkyloxy-, in another embodiment from hydrogen, fluorine, chlorine and $(C_1-C_4)$-alkyl-, and in another embodiment they are hydrogen or $(C_1-C_4)$-alkyl substituents.

In one embodiment, $R^{2c}$ is hydrogen and $R^{2a}$ and $R^{2b}$ independently of one another are selected from the group consisting of hydrogen, halogen, hydroxyl, $(C_1-C_4)$-alkyl-, $(C_1-C_4)$-alkyloxy-, $(C_1-C_4)$-alkyl-$S(O)_m$—, amino, nitro and cyano, where all alkyl groups independently of one another are optionally substituted by one or more fluorine substituents, as applies generally to alkyl groups. In one embodiment, $R^{2c}$ is hydrogen and $R^{2a}$ and $R^{2b}$, as defined in the general definition, are not located at the ring carbon atoms of the phenyl ring which are adjacent to the atom via which the phenyl is attached to the oxazolopyrimidine ring shown in formula I. In one embodiment, the further substituents $R^{2a}$ and $R^{2b}$ are selected from the group consisting of halogen, hydroxy, $(C_1-C_4)$-alkyl-, $(C_1-C_4)$-alkyloxy-, amino, cyano, in another embodiment from halogen, hydroxy, $(C_1-C_4)$-alkyl-, $(C_1-C_4)$-alkyloxy-, in another embodiment from halogen, $(C_1-C_4)$-alkyl- and $(C_1-C_4)$-alkyloxy-, in another embodiment from halogen and $(C_1-C_4)$-alkyl-, where in all these embodiments all alkyl groups independently of one another are optionally substituted by one or more fluorine substituents.

In one embodiment of the invention, the substituents $R^{2a}$, $R^{2b}$ independently of one another are selected from the group consisting of halogen, hydroxyl, $(C_1-C_4)$-alkyl-, $(C_1-C_4)$-alkyloxy-, $(C_1-C_4)$-alkyl-$S(O)_m$—, amino, nitro and cyano and $R^{2c}$ is hydrogen.

In one embodiment of the invention, the substituents $R^{2a}$, $R^{2b}$ independently of one another are selected from $(C_1-C_4)$-alkyl- and $R^{2c}$ is hydrogen.

In one embodiment of the invention, the substituents $R^{2a}$, $R^{2b}$ independently of one another are $(C_1-C_4)$-alkyl-, where $R^{2a}$ and $R^{2b}$ are attached in the 2- and 6-position at the phenyl ring and $R^{2c}$ is hydrogen.

In one embodiment of the invention, the substituents $R^{2a}$, $R^{2b}$ are methyl, where $R^{2a}$ and $R^{2b}$ are attached in the 2- and 6-position at the phenyl ring and $R^{2c}$ is hydrogen.

In one embodiment of the invention, $R^3$ is selected from the group consisting of $(C_1-C_6)$-alkyl, $(C_2-C_6)$-alkenyl and $(C_2-C_6)$-alkynyl, in another embodiment, $R^3$ is $(C_1-C_6)$-alkyl, in another embodiment, $R^3$ is $(C_2-C_5)$-alkyl, and in another embodiment, $R^3$ is $(C_1-C_4)$-alkyl. In another embodiment, $R^3$ is selected from the group consisting of $(C_1-C_6)$-alkyl, $(C_3-C_7)$-cycloalkyl-$C_uH_{2u}$— and Het-$C_vH_{2v}$—, in another embodiment from $(C_3-C_7)$-cycloalkyl-$C_uH_{2u}$— and Het-$C_vH_{2v}$—, in another embodiment, $R^3$ is $(C_3-C_7)$-cycloalkyl-$C_uH_{2u}$—, and in another embodiment, $R^3$ is Het-$C_vH_{2v}$—, where in this embodiment u and v independently of one another are selected from the group consisting of 1 and 2. In one embodiment, u is 1, in another embodiment, u is 2. In one embodiment, v is 1, in another embodiment, v is 2. In one embodiment, the group $(C_3-C_7)$-cycloalkyl-$C_uH_{2u}$— which represents $R^3$ is selected from the group consisting of cyclopropyl-$C_uH_{2u}$—, cyclobutyl-$C_uH_{2u}$— and cyclopentyl-$C_uH_{2u}$— and the group Het-$C_vH_{2v}$— which represents $R^3$ is tetrahydrofuranyl-$C_vH_{2v}$—. In one embodiment, $R^3$ is selected from the group consisting of cyclopropyl-$C_uH_{2u}$—, cyclobutyl-$C_uH_{2u}$— and cyclopentyl-$C_uH_{2u}$—.

In one embodiment, $R^3$ is selected from the group consisting of $(C_7-C_7)$-cycloalkyl-$C_uH_{2u}$— and Het-$C_vH_{2v}$—, or $R^3$ is a radical of a saturated or unsaturated, 3-membered to 10-membered, monocyclic or bicyclic ring which contains 0, 1, 2, 3 or 4 identical or different ring heteroatoms selected from the group consisting of N, O and S, wherein one or two of the ring nitrogen atoms may carry a hydrogen atom or a $(C_1-C_4)$-alkyl substituent and one or two of the ring sulfur atoms may carry one or two oxo groups, and where the radical of a ring is optionally substituted at one or more ring carbon atoms by identical or different substituents $R^{31}$, and in another embodiment $R^3$ is a radical of a saturated or unsaturated, 3-membered to 10-membered, monocyclic or bicyclic ring which contains 0, 1, 2, 3 or 4 identical or different ring heteroatoms selected from the group consisting of N, O and S, where one or two of the ring nitrogen atoms may carry a hydrogen atom or a $(C_1-C_4)$-alkyl substituent and one or two of the ring sulfur atoms may carry one or two oxo groups, and where the residue of a ring is optionally substituted at one or more ring carbon atoms by identical or different substituents $R^{31}$. In one embodiment, the number of ring heteroatoms in the ring representing $R^3$ is 0, 1, 2 or 3, in another embodiment 0, 1 or 2, in another embodiment 0 or 1, in another embodiment 0, in another embodiment it is 1, 2, 3 or 4, in another embodiment 1, 2 or 3, in another embodiment 1 or 2, in another embodiment 1. Thus, the radical of the ring which represents $R^3$ may be carbocyclic or heterocyclic. In one embodiment, the ring heteroatoms in $R^3$ are selected from the group consisting of N and O, in another embodiment from N and S, in another embodiment from O and S, in another embodiment they are N, where ring nitrogen atoms may carry a hydrogen atom or a $(C_1-C_4)$-alkyl substituent as occurs in saturated or partially unsaturated heterocycles or in 5-membered aromatic rings in heterocycles such as pyrrole or benzimidazole, for example, or may not carry a hydrogen atom or a $(C_1-C_4)$-alkyl substituent as occurs in aromatic heterocycles such as imidazole or pyridine, for example. In a radical of a heterocycle representing $R^3$ which contains one or more ring sulfur atoms, in one embodiment one of the ring sulfur atoms is non-oxidized or carries one or two oxo groups, and any other ring sulfur atoms are non-oxidized. The radical of a monocyclic or bicyclic ring representing $R^3$ may be bonded to the group A via any suitable ring carbon atom or ring nitrogen atom. In one embodiment it is bonded via a ring carbon atom, in another embodiment it is bonded via a ring carbon atom or, in case A is NH, via a ring nitrogen atom, and in another embodiment it is bonded via a ring nitrogen atom. The radical of a monocyclic or bicyclic ring representing $R^3$ may be unsaturated and in this case may contain 1, 2, 3, 4 or 5, or 1, 2, 3 or 4, or 1, 2 or 3, or 1 or 2, or 1, double bonds within the ring and may be aromatic or non-aromatic in any of the one or two rings, or it may be saturated and in this latter case contain no double bonds within the ring. In one embodiment, the radical of the ring representing $R^3$ is saturated or aromatic, in another embodiment it is saturated, and in another embodiment it is aromatic. In one embodiment, the radical of the 3-membered or 4-membered ring representing $R^3$ is saturated. If $R^3$ comprises ring nitrogen atoms which can carry a hydrogen atom or a $(C_1-C_4)$-alkyl substituent, one of such ring nitrogen atoms or two of such ring nitrogen atoms may be present. In one embodiment, the number of optional substituents $R^{31}$ on ring carbon atoms in the ring representing $R^3$ is 1, 2, 3, 4, 5 or 6, in another embodiment 1, 2, 3, 4 or 5, in another embodiment 1, 2, 3 or 4, in another embodiment 1, 2 or 3, in another embodiment 1 or 2, in another embodiment 1.

The ring which can represent $R^3$ may be 3-membered, 4-membered, 5-membered, 6-membered, 7-membered, 8-membered, 9-membered or 10-membered. In one embodiment, $R^3$ is 4-membered to 10-membered, in another embodiment 4-membered to 9-membered, in another embodiment 4-membered to 8-membered, in another embodiment 4-membered to 7-membered, in another embodiment 5-membered to 7-membered, in another embodiment 5-membered or 6-membered, in another embodiment 6-membered, in another embodiment 8-membered to 10-membered, in another embodiment 9-membered to 10-membered. In one embodiment, a 3-membered ring representing $R^3$ does not contain any ring heteroatoms. In one embodiment, $R^3$ is monocyclic, in another embodiment bicyclic. In one embodiment, a bicyclic group representing $R^3$ is at least 7-membered. Among others, the radical of a ring representing $R^3$ can be a cycloalkyl group, a phenyl group, a naphthyl group, a radical of an unsaturated, aromatic or non-aromatic heterocyclic group or a radical of a saturated heterocyclic group, which all are optionally substituted on ring carbon atoms and ring nitrogen atoms as specified with respect to $R^3$. As far as applicable, all explanations given above with respect to such groups apply correspondingly to $R^3$. Another example of groups which may represent $R^3$ are cycloalkenyl groups such as $(C_5-C_7)$-cycloalkenyl groups, which may be bonded via any ring carbon atom and are optionally substituted as specified with respect to $R^3$. In one embodiment, optional substituents $R^{31}$ on a cycloalkenyl group representing $R^3$ are selected from the group consisting of fluorine and $(C_1-C_4)$-alkyl.

In one embodiment, cycloalkenyl groups contain one double bond within the ring, which double bond may be present in any position. Examples of cycloalkenyl are cyclopentenyl including cyclopent-1-enyl, cyclopent-2-enyl and cyclopent-3-enyl, cyclohexenyl including cyclohex-1-enyl, cyclohex-2-enyl and cyclohex-3-enyl, and cycloheptenyl including cyclohept-1-enyl, cyclohept-2-enyl, cyclopent-3-enyl and cyclohept-4-enyl. Examples of radicals of rings from which $R^3$ is chosen in one embodiment of the invention are cyclopropyl, cyclobutyl, cyclopentyl, cyclohexyl, phenyl, oxetanyl including oxetan-3-yl, tetrahydrofuranyl including tetrahydrofuran-3-yl, tetrahydrothiophenyl including tetrahydrothiophen-3-yl, tetrahydropyranyl including tetrahydropyran-4-yl, azetidinyl including azetidin-1-yl, pyrrolidinyl, piperidinyl, imidazolidinyl, piperazinyl, morpholinyl including morpholin-1-yl, thiomorpholinyl, furanyl including furan-3-yl, thiophenyl including thiophen-3-yl, pyrazolyl including pyrazol-3-yl, imidazolyl, thiazolyl including thiazol-2-yl, pyridinyl including pyridin-2-yl, pyridin-3-yl and pyridin-4-yl, pyridazinyl including pyridazin-3-yl, where in all of them, if applicable, one or two of the ring nitrogen atoms may carry a hydrogen atom or $(C_1-C_4)$-alkyl, and where all of them are optionally substituted at one or more ring carbon atoms by identical or different substituents $R^{31}$, and where in all of them, if applicable, a ring sulfur atom may be non-oxidized, i.e. be present as a sulfur atom, or carry one or two oxo groups, i.e. be present in the form of a sulfoxide or sulfone.

In one embodiment, $R^3$ is selected from the group consisting of phenyl and a radical of a saturated or unsaturated 3-membered to 7-membered, monocyclic ring, in another embodiment from phenyl and a radical of a saturated or unsaturated 5-membered to 7-membered, monocyclic ring, in another embodiment from phenyl, pyridinyl and a radical of a saturated 3-membered to 7-membered, monocyclic ring, in another embodiment from phenyl, pyridinyl and a radical of a saturated 5-membered to 7-membered, monocyclic ring, in another embodiment from phenyl and a radical of a saturated 3-membered to 7-membered, monocyclic ring, in another embodiment from phenyl and a radical of a saturated 5-membered to 7-membered, monocyclic ring, where in all these embodiments the monocyclic ring contains 1 or 2 identical or different ring heteroatoms selected from the group consisting of N, O and S, where one or two of the ring nitrogen atoms may carry a hydrogen atom or a $(C_1-C_4)$-alkyl substituent and one or two of the ring sulfur atoms may carry one or two oxo groups, and where the phenyl, the pyridinyl and the radical of a ring are optionally substituted at one or more ring carbon atoms by identical or different substituents $R^{31}$, and where pyridinyl includes pyridin-2-yl, pyridin-3-yl and pyridin-4-yl. In another embodiment, $R^3$ is phenyl which is optionally substituted by one or more identical or different substituents $R^{31}$.

In one embodiment of the invention, $R^{31}$ is selected from the group consisting of halogen, $(C_1-C_4)$-alkyl, $(C_3-C_7)$-cycloalkyl, hydroxyl, $(C_1-C_4)$-alkyloxy, oxo, $(C_1-C_4)$-alkyl-S(O)$_m$—, amino, $(C_1-C_4)$-alkylamino, di($(C_1-C_4)$-alkyl)amino, $(C_1-C_4)$-alkylcarbonylamino, $(C_1-C_4)$-alkylsulfonylamino, cyano, $(C_1-C_4)$-alkylcarbonyl, aminosulfonyl, $(C_1-C_4)$-alkylaminosulfonyl and di($(C_1-C_4)$-alkyl)aminosulfonyl, in another embodiment from halogen, $(C_1-C_4)$-alkyl, $(C_3-C_7)$-cycloalkyl, hydroxyl, $(C_1-C_4)$-alkyloxy, oxo, $(C_1-C_4)$-alkyl-S(O)$_m$—, amino, $(C_1-C_4)$-alkylamino, di($(C_1-C_4)$-alkyl)amino, cyano, aminosulfonyl, $(C_1-C_4)$-alkylaminosulfonyl and di($(C_1-C_4)$-alkyl)aminosulfonyl, in another embodiment from halogen, $(C_1-C_4)$-alkyl, $(C_3-C_7)$-cycloalkyl, hydroxyl, $(C_1-C_4)$-alkyloxy, oxo, $(C_1-C_4)$-alkyl-S(O)$_m$—, amino, $(C_1-C_4)$-alkylamino, di($(C_1-C_4)$-alkyl)amino, cyano and aminosulfonyl, in another embodiment from halogen, $(C_1-C_4)$-alkyl, $(C_3-C_7)$-cycloalkyl, hydroxyl, $(C_1-C_4)$-alkyloxy, oxo, amino, $(C_1-C_4)$-alkylamino, di($(C_1-C_4)$-alkyl)amino, cyano and aminosulfonyl, in another embodiment from halogen, $(C_1-C_4)$-alkyl, $(C_3-C_7)$-cycloalkyl, hydroxyl, $(C_1-C_4)$-alkyloxy, oxo, amino, $(C_1-C_4)$-alkylamino and di($(C_1-C_4)$-alkyl)amino, in another embodiment from halogen, $(C_1-C_4)$-alkyl, $(C_3-C_7)$-cycloalkyl, hydroxyl and $(C_1-C_4)$-alkyloxy, in another embodiment from halogen, $(C_1-C_4)$-alkyl and $(C_1-C_4)$-alkyloxy, in another embodiment from fluorine, chlorine, $(C_1-C_4)$-alkyl, $(C_3-C_7)$-cycloalkyl, hydroxyl and $(C_1-C_4)$-alkyloxy, where in all these embodiments all alkyl groups independently of one another are optionally substituted by one or more fluorine substituents.

In one embodiment, the optional substituents $R^{31}$ at the radical of an aromatic ring which represents $R^3$, for example at a phenyl group or pyridinyl group which represents $R^3$, are selected from the group consisting of halogen, $(C_1-C_4)$-alkyl, $(C_3-C_7)$-cycloalkyl, hydroxyl, $(C_1-C_4)$-alkyloxy, $(C_1-C_4)$-alkyl-S(O)$_m$—, amino, $(C_1-C_4)$-alkylamino, di($(C_1-C_4)$-alkyl)amino, $(C_1-C_4)$-alkylcarbonylamino, $(C_1-C_4)$-alkylsulfonylamino, cyano, $(C_1-C_4)$-alkylcarbonyl, aminosulfonyl, $(C_1-C_4)$-alkylaminosulfonyl and di($(C_1-C_4)$-alkyl)aminosulfonyl, in another embodiment from halogen, $(C_1-C_4)$-alkyl, $(C_3-C_7)$-cycloalkyl, hydroxyl, $(C_1-C_4)$-alkyloxy, $(C_1-C_4)$-alkyl-S(O)$_m$—, amino, $(C_1-C_4)$-alkylamino, di($(C_1-C_4)$-alkyl)amino, cyano, aminosulfonyl, $(C_1-C_4)$-alkylaminosulfonyl and di($(C_1-C_4)$-alkyl)aminosulfonyl, in another embodiment from halogen, $(C_1-C_4)$-alkyl, $(C_3-C_7)$-cycloalkyl, hydroxyl, $(C_1-C_4)$-alkyloxy, $(C_1-C_4)$-alkyl-S(O)$_m$—, amino, $(C_1-C_4)$-alkylamino, di($(C_1-C_4)$-alkyl)amino, cyano and aminosulfonyl, in another embodiment from halogen, $(C_1-C_4)$-alkyl, $(C_3-C_7)$-cycloalkyl, hydroxyl, $(C_1-C_4)$-alkyloxy, amino, $(C_1-C_4)$-alkylamino, di($(C_1-C_4)$-alkyl)amino, cyano and aminosulfonyl, in another embodiment from halogen, $(C_1-C_4)$-alkyl, $(C_3-C_7)$-cycloalkyl, hydroxyl, $(C_1-C_4)$-alkyloxy, amino, $(C_1-C_4)$-alkylamino and di($(C_1-C_4)$-alkyl)amino, in another embodiment from halogen, $(C_1-C_4)$-alkyl, $(C_3-C_7)$-cycloalkyl, $(C_1-C_4)$-alkyloxy and di($(C_1-C_4)$-alkyl)amino, in another embodiment from halogen, $(C_1-C_4)$-alkyl, $(C_3-C_7)$-cycloalkyl, hydroxyl and $(C_1-C_4)$-alkyloxy, in another embodiment from halogen, $(C_1-C_4)$-alkyl and $(C_1-C_4)$-alkyloxy, in another embodiment from fluorine, chlorine, $(C_1-C_4)$-alkyl, $(C_3-C_7)$-cycloalkyl, hydroxyl and $(C_1-C_4)$-alkyloxy, where in all these embodiments all alkyl groups independently of one another are optionally substituted by one or more fluorine substituents.

In one embodiment, the optional substituents $R^{31}$ at the radical of a saturated or non-aromatic unsaturated ring which represents $R^3$ are selected from the group consisting of halogen, $(C_1-C_4)$-alkyl, $(C_3-C_7)$-cycloalkyl, hydroxyl, $(C_1-C_4)$-alkyloxy, oxo, $(C_1-C_4)$-alkyl-S(O)$_m$—, amino, $(C_1-C_4)$-alkylamino, di($(C_1-C_4)$-alkyl)amino, $(C_1-C_4)$-alkylcarbonylamino, $(C_1-C_4)$-alkylsulfonylamino and cyano, in another embodiment from halogen, $(C_1-C_4)$-alkyl, $(C_3-C_7)$-cycloalkyl, hydroxyl, $(C_1-C_4)$-alkyloxy, oxo, amino, $(C_1-C_4)$-alkylamino, di($(C_1-C_4)$-alkyl)amino and cyano, in another embodiment from halogen, $(C_1-C_4)$-alkyl, $(C_3-C_7)$-cycloalkyl, hydroxyl, $(C_1-C_4)$-alkyloxy and oxo, in another embodiment from halogen, $(C_1-C_4)$-alkyl, hydroxyl, $(C_1-C_4)$-alkyloxy and oxo, in another embodiment from fluorine, chlorine, $(C_1-C_4)$-alkyl, hydroxyl, $(C_1-C_4)$-alkyloxy and oxo, in another embodiment from $(C_1-C_4)$-alkyl, hydroxyl and oxo, in another embodiment from alkyl and hydroxyl, and in another embodiment they are $(C_1-C_4)$-alkyl, where in all these embodiments all alkyl groups independently of one another are optionally substituted by one or more fluorine substituents. If the radical of a ring representing $R^3$ contains any oxo groups as substituents $R^{31}$, in one embodiment not more than two such oxo substituents are present, and in another embodiment not more than one such oxo substituent is present.

In one embodiment of the invention, the ring heteroatoms in Het are selected from the group consisting of N and O, in another embodiment from O and S, in another embodiment they are O atoms. In another embodiment, the number of ring heteroatoms in Het is 1. In one embodiment, two ring oxygen atoms in Het are not present at adjacent ring positions, in another embodiment two ring heteroatoms selected from the group consisting of O and S are not present at adjacent ring positions, in another embodiment, two ring heteroatoms are not present at adjacent ring positions. Ring nitrogen atoms in Het carry a hydrogen atom or a substituent as indicated. In one embodiment, optional substituents at ring nitrogen atoms in Het are $(C_1-C_4)$-alkyl substituents. In one embodiment, optional substituents at ring nitrogen atoms and ring carbon atoms in Het are $(C_1-C_4)$-alkyl substituents. In one embodiment, the number of optional substituents on Het is 1, 2, 3, 4 or 5, in another embodiment 1, 2, 3 or 4, in another embodiment 1, 2 or 3, in another embodiment 1 or 2, in another embodiment 1. Het may be attached via any suitable ring carbon atom. In one embodiment, Het is attached via a ring carbon atom which is not adjacent to a ring heteroatom. Het may be 4-membered, 5-membered, 6-membered or 7-membered. In one embodiment, Het is 4-membered or 5-membered, in another embodiment 5-membered to 7-membered, in another embodiment 5-membered or 6-membered, in another embodiment 4-membered. Examples of Het from which Het is selected in one embodiment are oxetanyl including oxetan-2-yl and oxetan-3-yl, tetrahydrofuranyl including tetrahydrofuran-2-yl and tetrahydrofuran-3-yl, tetrahydropyranyl including tetrahydropyran-2-yl, tetrahydropyran-3-yl and tetrahydropyran-4-yl, oxepanyl including oxepan-2-yl, oxepan-3-yl and oxepan-4-yl, [1,3]dioxolanyl including [1,3]dioxolan-2-yl and [1,3]dioxolan-4-yl, [1,4]dioxanyl including [1,4]dioxan-2-yl, thietanyl including thietan-2-yl and thietan-3-yl, tetrahydrothiophenyl including tetrahydrothiophen-2-yl and tetrahydrothiophen-3-yl, tetrahydrothiopyranyl including tetrahydrothiopyran-2-yl, tetrahydrothiopyran-3-yl and tetrahydrothiopyran-4-yl, [1,4]dithianyl including [1,4]dithian-2-yl, azetidinyl including azetidin-2-yl and azetidin-3-yl, pyrrolidinyl including pyrrolidin-2-yl and pyrrolidin-3-yl, piperidinyl including piperidin-2-yl, piperidin-3-yl and piperidin-4-yl, azepanyl including azepan-2-yl, azepan-3-yl and azepan-4-yl, oxazolidinyl including oxazolidin-2-yl, oxazolidin-4-yl and oxazolidin-5-yl, thiazolidinyl including thiazolidin-2-yl, thiazolidin-4-yl and thiazolidin-5-yl, morpholinyl including morpholin-2-yl and morpholin-3-yl, thiomorpholinyl including thiomorpholin-2-yl and thiomorpholin-3-yl, all of which are optionally substituted as indicated with respect to Het.

The invention provides all compounds of the formula I wherein any one or more structural elements such as groups, substituents and numbers are defined as in any of the specified embodiments or definitions of the elements or have any one or more of the specific meanings which are mentioned herein as examples of elements, wherein all combinations of one or more specified embodiments and/or definitions and/or specific meanings of the elements are a subject of the present invention. Also with respect to all such compounds of the formula I, all their stereoisomeric forms and mixtures of stereoisomeric forms in any ratio, and their physiologically acceptable salts, and the physiologically acceptable solvates of any of them, are a subject of the present invention.

An example of compounds according to the invention which with respect to any structural elements are defined as in the specified embodiments of the invention or definitions of such elements, and which form part of the subject matter of the invention, are compounds of the formula I in which $R^3$ is selected from the group consisting of $(C_1-C_6)$-alkyl, $(C_3-C_7)$-cycloalkyl-$C_uH_{2u}$— and Het-$C_vH_{2v}$—, where u and v are selected from the group consisting of 1 and 2, or $R^3$ is a radical of a saturated or unsaturated 3-membered to 10-membered monocyclic or bicyclic ring which contains 0, 1 or 2 identical or different ring heteroatoms selected from the group consisting of N, O and S, where one or two of the ring nitrogen atoms may carry a hydrogen atom or a $(C_1-C_4)$-alkyl substituent and one of the ring sulfur atoms may carry one or two oxo groups and where the radical of a ring is optionally substituted at one or more ring carbon atoms by identical or different substituents $R^{31}$;

Het is a radical of a saturated 4-membered to 6-membered monocyclic heterocycle which contains 1 ring heteroatom selected from the group consisting of N, O and S and which is attached via a ring carbon atom, where the radical of a heterocycle is optionally substituted by one or more identical or different substituents selected from the group consisting of fluorine and $(C_1-C_4)$-alkyl;

and all other groups and numbers are defined as in the general definition of the compounds of the formula I or one of the indicated embodiments of the invention or definitions of structural elements.

A further embodiment relates to compounds of the formula I in which one or more radicals have the following meanings:
A is O or S;
X is $(C_3-C_7)$-cycloalkanediyl;
$R^{2a}$, $R^{2b}$ and $R^{2c}$ independently of one another are hydrogen, halogen, hydroxyl, $(C_1-C_4)$-alkyloxy, $(C_1-C_4)$-alkyl-S$(O)_m$—, amino, nitro or cyano;
$R^1$ is hydrogen or $(C_1-C_4)$-alkyl;
$R^3$ $(C_1-C_6)$-alkyl, $(C_3-C_7)$-cycloalkyl-$C_uH_{2u}$— or Het-$C_vH_{2v}$—, where u and v are selected from the group consisting of 1 and 2, or $R^3$ is a radical of a saturated or unsaturated 3-membered to 10-membered monocyclic or bicyclic ring which contains 0, 1 or 2 identical or different ring heteroatoms selected from the group consisting of N, O and S, where one or two of the ring nitrogen atoms may carry a hydrogen atom or a $(C_1-C_4)$-alkyl substituent and one of the ring sulfur atoms may carry one or two oxo groups and where the radical of a ring is optionally substituted at one or more ring carbon atoms by identical or different substituents $R^{31}$;
$R^{31}$ is halogen, $(C_1-C_4)$-alkyl, $(C_3-C_7)$-cycloalkyl, hydroxyl, $(C_1-C_4)$-alkyloxy, oxo, $(C_1-C_4)$-alkyl-S$(O)_m$—, amino, $(C_1-C_4)$-alkylamino, di$((C_1-C_4)$-alkyl)amino, $(C_1-C_4)$-alkylcarbonylamino, $(C_1-C_4)$-alkylsulfonylamino, nitro, cyano, $(C_1-C_4)$-alkylcarbonyl, aminosulfonyl, $(C_1-C_4)$-alkylaminosulfonyl or di$((C_1-C_4)$-alkyl)aminosulfonyl;
Het is a radical of a saturated 4-membered to 6-membered monocyclic heterocycle which contains 1 ring heteroatom selected from the group consisting of N, O and S and which is attached via a ring carbon atom, where the radical of a heterocycle is optionally substituted by one or more identical or different substituents selected from the group consisting of fluorine and $(C_1-C_4)$-alkyl;
m is 0, 1 or 2;
where all cycloalkyl and cycloalkanediyl groups independently of one another and independently of other substituents are optionally substituted by one or more identical or different substituents selected from the group consisting of fluorine and $(C_1-C_4)$-alkyl;
where all alkyl, alkanediyl, $C_uH_{2u}$, $C_vH_{2v}$, $C_zH_{2z}$, alkenyl, alkenediyl, alkynyl and alkynediyl groups independently of one another and independently of other substituents may optionally be substituted by one or more fluorine substituents.

A further embodiment relates to compounds of the formula I in which one or more radicals have the following meanings:
A is O;
X is ($C_3$-$C_7$)-cycloalkanediyl;
$R^1$ is hydrogen;
$R^{2a}$, $R^{2b}$ and $R^{2c}$ independently of one another are hydrogen, halogen, hydroxyl, ($C_1$-$C_4$)-alkyl or ($C_1$-$C_4$)-alkyloxy;
$R^3$ is ($C_1$-$C_6$)-alkyl, ($C_3$-$C_7$)-cycloalkyl-$C_uH_{2u}$— or Het-$C_vH_{2v}$—, where u and v are selected from the group consisting of 0 and 1, or $R^3$ is a radical of a saturated or unsaturated 3-membered to 7-membered monocyclic or bicyclic ring which contains 0, 1 or 2 identical or different ring heteroatoms selected from the group consisting of N, O and S, where one or two of the ring nitrogen atoms may carry a hydrogen atom or a ($C_1$-$C_4$)-alkyl substituent and one of the ring sulfur atoms may carry one or two oxo groups and where the radical of a ring is optionally substituted at one or more ring carbon atoms by identical or different substituents $R^{31}$;
$R^{31}$ is halogen, ($C_1$-$C_4$)-alkyl, ($C_3$-$C_7$)-cycloalkyl, hydroxyl or ($C_1$-$C_4$)-alkyloxy;
Het is a radical of a saturated 4-membered to 6-membered monocyclic heterocycle which contains 1 ring heteroatom selected from the group consisting of O and S and which is attached via a ring carbon atom, where the radical of a heterocycle is optionally substituted by one or more identical or different substituents selected from the group consisting of fluorine and ($C_1$-$C_4$)-alkyl;
where all alkyl, cycloalkanediyl, $C_uH_{2u}$ and $C_vH_{2v}$ groups independently of one another and independently of other substituents are optionally substituted by one or more fluorine substituents.

A further embodiment relates to compounds of the formula I in which one or more radicals have the following meanings:
A is O;
X is ($C_3$-$C_7$)-cycloalkanediyl;
$R^1$ is hydrogen;
$R^{2a}$, $R^{2b}$ and $R^{2c}$ independently of one another are hydrogen, halogen, hydroxyl, ($C_1$-$C_4$)-alkyl or ($C_1$-$C_4$)-alkyloxy;
$R^3$ is a radical of a saturated or unsaturated, 3-membered to 7-membered, monocyclic ring which contains 0 or 1 ring heteroatom selected from the group consisting of N, O and S, where a ring nitrogen atom may carry a hydrogen atom or a ($C_1$-$C_4$)-alkyl substituent and a ring sulfur atom may carry one or two oxo groups and where the radical of a ring is optionally substituted at one or more ring carbon atoms by identical or different substituents $R^{31}$;
$R^{31}$ is halogen, ($C_1$-$C_4$)-alkyl, ($C_3$-$C_7$)-cycloalkyl, hydroxyl or ($C_1$-$C_4$)-alkyloxy; where all cycloalkyl groups independently of one another and independently of other substituents are optionally substituted by one or more identical or different substituents selected from the group consisting of fluorine and ($C_1$-$C_4$)-alkyl; where all alkyl and cycloalkanediyl groups independently of one another and independently of other substituents are optionally substituted by one or more fluorine substituents.

A further embodiment relates to compounds of the formula I in which one or more radicals have the following meanings:
A is O;
X is ($C_3$-$C_7$)-cycloalkanediyl;
$R^1$ is hydrogen;
$R^{2c}$ is hydrogen;
$R^{2a}$ and $R^{2b}$ independently of one another are ($C_1$-$C_4$)-alkyl;
$R^3$ is phenyl, where the phenyl ring is optionally substituted at one or more ring carbon atoms by identical or different substituents $R^{31}$;
$R^{31}$ is halogen, ($C_1$-$C_4$)-alkyl, ($C_3$-$C_7$)-cycloalkyl, hydroxyl or ($C_1$-$C_4$)-alkyloxy; where all cycloalkyl groups independently of one another and independently of other substituents are optionally substituted by one or more identical or different substituents selected from the group consisting of fluorine and ($C_1$-$C_4$)-alkyl; where all alkyl and cycloalkanediyl groups independently of one another and independently of other substituents are optionally substituted by one or more fluorine substituents.

A further embodiment relates to compounds of the formula I in which one or more radicals have the following meanings:
A is O;
X is ($C_3$-$C_7$)-cycloalkanediyl;
$R^1$ is hydrogen;
$R^{2c}$ is hydrogen;
$R^{2a}$ and $R^{2b}$ independently of one another are ($C_1$-$C_4$)-alkyl, where $R^{2a}$ and $R^{2b}$ are attached at positions 2 and 6 of the phenyl ring;
$R^3$ is phenyl, where the phenyl ring is optionally substituted at one or more ring carbon atoms by identical or different substituents $R^{31}$;
$R^{31}$ is halogen.

Likewise, also with respect to all specific compounds disclosed herein, such as the example compounds which represent embodiments of the invention wherein the various groups and numbers in the general definition of the compounds of the formula I have the specific meanings present in the respective specific compound, it applies that they are a subject of the present invention in any of their stereoisomeric forms and/or a mixture of stereoisomeric forms in any ratio, and in the form of their physiologically acceptable salts, and in the form of the physiologically acceptable solvates of such compounds or such salts. Irrespective of whether a specific compound is disclosed herein as a free compound and/or as a specific salt, the invention provides the compound both in the form of the free compound and in the form of all its physiologically acceptable salts, and if a specific salt is disclosed, additionally in the form of this specific salt, and in the form of the physiologically acceptable solvates of such a compound or such salts. Thus, the invention also provides a compound of the formula I which is chosen from any one or more of the specific compounds of the formula I disclosed herein, including the example compounds specified below, and the physiologically acceptable salts thereof, and the physiologically acceptable solvates of such a compound or such salts, wherein the invention provides the compound of the formula I in any of its stereoisomeric forms or as a mixture of stereoisomeric forms in any ratio, if applicable. An example which may be mentioned is a compound of the formula I or a physiologically acceptable solvate thereof, selected from the group consisting of 3-{4-[5-(2-fluorophenoxy)-oxazolo[5,4-d]pyrimidin-2-yl]-2,6-dimethylphenoxy}cyclobutanecarboxylic acid 3-{4-[5-(3-chlorophenoxy)oxazolo[5,4-d]pyrimidin-2-yl]-2,6-dimethylphenoxy}cyclobutanecarboxylic acid where the invention provides a compound such as, for example, 3-{4-[5-(2-fluorophenoxy)oxazolo[5,4-d]pyrimidin-2-yl]-2,6-dimethylphenoxy}cyclobutanecarboxylic acid or 3-{4-[5-(3-chlorophenoxy)oxazolo[5,4-d]pyrimidin-2-yl]-2,6-dimethylphenoxy}cyclobutanecarboxylic acid, which may be present in the cis configuration or the trans configuration, in the cis configuration and in the trans configuration and as a mixture of the isomeric forms in any ratio.

Another subject of the present invention are processes for the preparation of the compounds of the formula I and their salts and solvates, by which the compounds are obtainable and which are outlined in the following. In one process, a compound of the formula II is reacted with a compound of the formula III to give a compound of the formula I

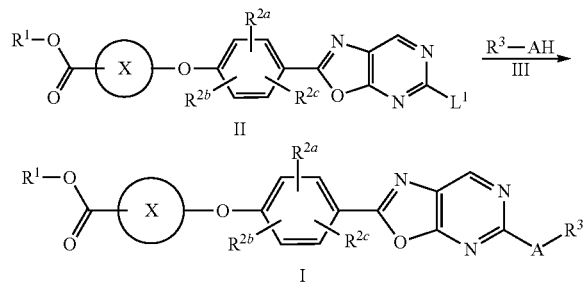

where the groups A, X, $R^1$, $R^{2a}$, $R^{2b}$, $R^{2c}$ and $R^3$ in the compounds of the formulae II and III are defined as in the compounds of the formula I and additionally functional groups can be present in protected form or in the form of a precursor group which is later converted into the final group. The group $L^1$ in the compounds of the formula II is a leaving group which can be replaced in a nucleophilic aromatic substitution reaction, such as a halogen atom, for example chlorine or bromine, or a sulfoxide group or a sulfone group, for example a group of the formula —S(O)-Alk or —S(O)$_2$-Alk where Alk is a ($C_1$-$C_4$)-alkyl group, for example methyl or ethyl.

The reaction of the compounds of the formulae II and III is a nucleophilic aromatic substitution reaction at the carbon atom in position 5 of the oxazolo[5,4-d]pyrimidine ring, i.e. in the pyrimidine grouping, and can be carried out under standard conditions for such reactions, which are well known to the person skilled in the art. In general, the reaction is, depending on the particular circumstances of the case in question, carried out in an inert solvent, for example a hydrocarbon or a chlorinated hydrocarbon such as benzene, toluene, xylene, chlorobenzene, dichloromethane, chloroform or dichloroethane, an ether such as tetrahydrofuran (THF), dioxane, dibutyl ether, diisopropyl ether or 1,2-dimethoxyethane (DME), a ketone such as acetone or butan-2-one, an ester such as ethyl acetate or butyl acetate, a nitrile such as acetonitrile, an amine such as N,N-dimethylformamide (DMF), N,N-dimethylacetamide (DMA) or N-methylpyrrolidin-2-one (NMP), or a mixture of solvents, at temperatures of from about 20° C. to about 160° C., for example at temperatures of from about 40° C. to about 100° C. In general, it is favorable to add a base to increase the nucleophilicity of the compound of the formula III, for example a tertiary amine, such as triethylamine, ethyldiisopropylamine or N-methylmorpholine, or an inorganic base such as an alkaline earth metal hydride, hydroxide, carbonate or bicarbonate such as sodium hydride, sodium hydroxide, potassium hydroxide, sodium carbonate, potassium carbonate, cesium carbonate or sodium bicarbonate or an alkoxide or amide such as sodium methoxide, sodium ethoxide, potassium methoxide, potassium tert-butoxide, sodium amide or lithium diisopropylamide. Prior to the reaction with the compound of the formula II, a compound of the formula III may also separately be treated with a base and converted into a salt.

The starting materials of the formulae II and III can be obtained by processes described in the literature or analogously to processes described in the literature, and in many cases they are commercially available. The compounds of the formula II can be obtained, for example, by reacting a 5-aminopyrimidine derivative of the formula IV with an activated carboxylic acid derivative of the formula V to give a compound of the formula VI, cyclizing the latter compound with formation of the oxazolo[5,4-d]pyrimidine ring system to give a compound of the formula VII, and introducing the grouping $R^1O$—C(O)—X— into the compound of the formula VII by reaction with a compound of the formula VIII to give a compound of the formula IX which, depending on the meaning of R' and $L^1$, may already be a compound of the formula II, and optionally modifying the group R' in the compound of the formula IX, giving a compound of the formula II.

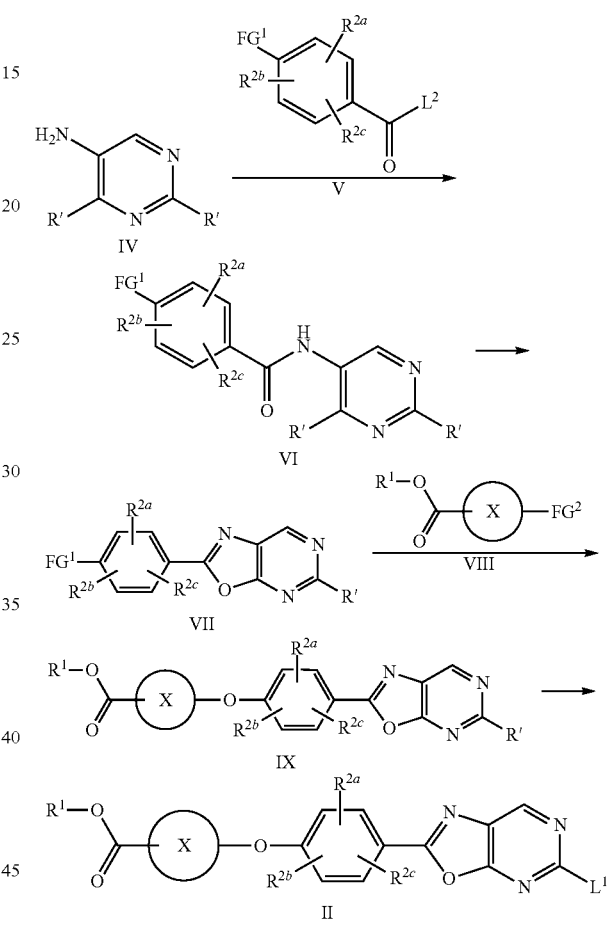

The groups X, $R^1$, $R^{2a}$, $R^{2b}$ and $R^{2c}$ in the compounds of the formulae V, VI, VIII and IX are defined as in the compounds of the formula I and additionally functional groups can be present in protected form or in the form of a precursor group which is later converted into the final group. The oxygen atom between ring X and the phenylene group is a component either of group $FG^1$ or of group $FG^2$ in the compounds of the formulae VII and VIII, such that after the reaction of the compounds of the formulae VII and VIII any parts of the groups $FG^1$ and $FG^2$ remaining in the compound of the formula IX together form the desired ether. Thus, for example, the group $FG^2$ may be a hydroxyl group, and the group $FG^1$ in the compound of the formula VII is likewise a hydroxyl group whose oxygen atom together with the alkanediyl moiety then, after etherification of the compound of the formula VII with the compound of the formula VIII, forms the desired alkanediyloxy group.

The groups $FG^1$ and $FG^2$ in the compounds of the formulae V, VI, VII and VIII are functional groups which are suitable for the coupling type used for forming the desired ether from the part of groups $FG^1$ and $FG^2$ remaining in the compound of the formula IX. If, for example, the group X is attached via a nucleophilic substitution reaction to an oxygen atom in the group $FG^1$ in formula VII, as mentioned above, $FG^2$ may be a leaving group such as a halogen atom such as chlorine, bromine or iodine, or a sulfonyloxy group such as methanesulfonyloxy, trifluoromethanesulfonyloxy or toluenesulfonyloxy.

The group $FG^1$ in the compounds of the formulae V, VI and VII may also be present in protected form or in the form of a precursor group which is at a later point converted into the group which in the compound of the formula VII reacts with the compound of the formula VIII. Thus, for example, a hydroxyl group which represents $FG^1$ in the compound of the formula VII may be present in protected form in the compounds of the formulae V and VI, for example in the form of an etherified hydroxyl group such as a benzyl ether or an alkyl ethers such as a methyl ether. Such ethers can be cleaved using methods which are well-known to the person skilled in the art. A summary of methods to remove protective groups can be found in the literature, for example in P. J. Kocienski, Protecting Groups (Thieme Verlag, 1994), or T. W. Greene and P. G. M. Wuts, Protective Groups in Organic Synthesis (John Wiley & Sons, 1999).

The group $L^2$ in the compounds of the formula V may be a nucleophilically substitutable leaving group and may in particular be a halogen atom, such as chlorine or bromine, and the compound of the formula V may thus be a carbonyl halide. The compound of the formula V may also be a carboxylic anhydride, for example. The groups R' in the compounds of the formulae IV, VI and IX may be a hydroxyl group or a halogen atom, such as chlorine and bromine. Compounds encountered in the synthesis of the compounds of the formula I, such as the compound of the formula IV, may also be present in another tautomeric form, for example in the keto form, provided the groups R' in the compound of the formula IV are hydroxyl groups. Compounds encountered in the synthesis of the compounds of the formula I, including starting materials, intermediates and products, may also be employed or obtained in the form of a salt.

The reaction of the compound of the formulae IV and V can be carried out under standard conditions for the acylation of an amine with an activated carboxylic acid derivative such as an acid halide or anhydride. In general, the reaction is carried out in an inert solvent, for example a hydrocarbon or a chlorinated hydrocarbon such as benzene, toluene, xylene, chlorobenzene, dichloromethane, chloroform or dichloroethane, an ether such as THF, dioxane, dibutyl ether, diisopropyl ether or DME, a ketone such as acetone or butan-2-one, an ester such as ethyl acetate or butyl acetate, or water, or a mixture of solvents, at temperatures of from about −10° C. to about 40° C., for example at temperatures of from about 0° C. to about 30° C. In general, the reaction is carried out with addition of a base, for example a tertiary amine, such as triethylamine, ethyldiisopropylamine or N-methylmorpholine or an inorganic base such as an alkali metal hydroxide, carbonate or bicarbonate such as sodium hydroxide, potassium hydroxide, sodium carbonate, potassium carbonate or sodium bicarbonate. The reaction of the compounds of the formulae VI and VII is generally carried out in an inert solvent, for example an alcohol such as methanol, ethanol or isopropanol, or an ether such as THF, dioxane or DME, or a mixture of solvents, at temperatures of from about 20° C. to about 80° C., for example temperatures of about 40° C. to about 80° C., in the presence of a base, for example an alkoxide such as sodium methoxide, sodium ethoxide, potassium methoxide or potassium tert-butoxide.

If the group R' in the compound of the formula VI is hydroxyl, the cyclization of the compound of the formula VI to the compound of the formula VII can favorably be carried out in the presence of a halogenating agent such as a phosphorus halide, such as phosphorus pentachloride or phosphorus oxychloride or a mixture thereof, in an inert solvent, for example a hydrocarbon or a chlorinated hydrocarbon such as benzene, toluene, xylene, chlorobenzene, dichloromethane, chloroform or dichloroethane, at temperatures of from about 20° C. to about 100° C., for example at temperatures of from about 50° C. to about 80° C. If the group R' in the compound of the formula VI is halogen such as chlorine, the cyclization of the compound of the formula VI to the compound of the formula VII can be carried out thermally, for example by heating the compound of the formula VI in an inert solvent such as a hydrocarbon or a chlorinated hydrocarbon, for example toluene, xylene or chlorobenzene, or an amide, for example DMF, DMA or NMP, or a nitrile, for example acetonitrile, at temperatures of from about 100° C. to about 200° C., for example at temperatures of from about 120° C. to about 180° C., optionally under pressure and optionally in the presence of a base such as a tertiary amine, for example triethylamine, ethyldiisopropylamine or N-methylmorpholine, or an inorganic base, for example an alkali metal hydroxide, carbonate or bicarbonate such as sodium hydroxide, potassium hydroxide or sodium carbonate, potassium carbonate or sodium bicarbonate. Expediently, the thermal cyclization can be carried out in a microwave reactor.

The coupling of compounds of the formula VIII with compounds of the formula VII can be carried out using reactions of various types, as already mentioned above, for example via an alkylation reaction. Thus, the phenylene group in the compound VII can, for example when it carries a hydroxyl group which represents $FG^1$, be alkylated using a compound of the formula VIII in which $FG^2$ is a leaving group suitable for nucleophilic substitution reactions such as a halogen atom such as chlorine, bromine or iodine, or a sulfonyloxy group such as methanesulfonyloxy or toluenesulfonyloxy. The nucleophilic substitution reaction at the carbon atom of the compound of the formula VIII which carries the group $FG^2$ can be carried out under standard conditions for such reactions, which are well-known to the person skilled in the art. In general, the reaction is, depending on the particular circumstances of the case in question, carried out in an inert solvent, for example a hydrocarbon or a chlorinated hydrogen such as benzene, toluene, xylene, chlorobenzene, dichloromethane, chloroform or dichloroethane, an ether such as THF, dioxane, dibutyl ether, diisopropyl ether or DME, an alcohol such as methanol, ethanol or isopropanol, a ketone such as acetone or butan-2-one, an ester such as ethyl acetate or butyl acetate, a nitrile such as acetonitrile, an amide such as N,N-dimethylformamide or N-methylpyrrolidin-2-one, or a mixture of solvents, at temperatures of from about 20° C. to about 100° C., for example at temperatures of from about 40° C. to about 80° C. In general, it is favorable to add a base to increase the nucleophilicity of the compound of the formula XIII and/or to bind an acid released during the reaction, for example a base, for example a tertiary amine, such as triethylamine, ethyldiisopropylamine or N-methylmorpholine, or an inorganic base such as an alkali metal hydride, hydroxide, carbonate or bicarbonate such as sodium hydride, sodium hydroxide, potassium hydroxide, sodium carbonate, potassium carbonate, cesium carbonate or sodium bicarbonate or an alkoxide or amide such as sodium methoxide, sodium ethoxide, potassium methoxide, potassium tert-butoxide, sodium amide or lithium diisopropylamide. Prior to the reaction with the compound of the formula VIII, a compound of the formula VII in which FG¹ is hydroxyl may also separately be treated with a base and converted into a salt. A compound of the formula VII in which FG¹ is hydroxyl may be converted into a compound of the formula IX not only by reaction with a compound of the formula VIII in which FG² is a leaving group as indicated, but also by reaction with the corresponding alcohol, i.e. with a compound of the formula VIII in which FG² is hydroxyl, under the conditions of the Mitsunobu reaction in the presence of an azodicarboxylate such as diethyl azodicarboxylate or diisopropyl azodicarboxylate and a phosphine such as triphenylphosphine or tributylphosphine in an inert aprotic solvent, for example an ether such as THF or dioxane (see O. Mitsunobu, Synthesis (1981), 1-28).

The compound of the formula IX may already be a compound of the formula II and be employed in the reaction with the compound of the formula III if it has been obtained from a compound of the formula VI in which R' is halogen, such as chlorine, and the halogen atom in the cyclization product has not been replaced during the course of the synthesis, for example by a hydroxyl group during work-up, or if it has been obtained from a compound of the formula VI in which R' is hydroxyl, and simultaneously with the cyclization the second hydroxyl group in the compound of the formula VI is halogenated, for example replaced by a chlorine atom, as may be the case during the cyclization with the aid of a phosphorus halide. If the cyclization product obtained is a compound of the formula VII in which R' is hydroxyl, the hydroxyl group in the compound of the formula IX can be converted under standard conditions into a leaving group, for example by treatment with a halogenating agent such as a phosphorus halide into a halogen atom such as a chlorine atom or by treatment with a sulfonyl chloride or sulfonic anhydride into a sulfonyloxy group, according to what was stated above. Depending on the particular circumstances of the specific case, such as the reactivity of the specific compound of the formula III to be reacted with the compound of the formula II, it may also be advantageous to modify the group R' in a compound of the formula IX, even if it already is a leaving group. Thus, for example, a compound of the formula IX, in which R' is halogen, such as chlorine, may be converted by treatment with an alkanesulfinic acid of the formula Alk-S(O)—OH in which Alk is $(C_1-C_4)$-alkyl into a compound of the formula II in which L¹ is the group —S(O)₂-Alk, which is then reacted with a compound of the formula III. Such a reaction is generally carried out in the presence of a base such as an alkali metal hydride, hydroxide, carbonate or bicarbonate such as sodium hydride, sodium hydroxide, potassium hydroxide, sodium carbonate, potassium carbonate, cesium carbonate or sodium bicarbonate, in an inert solvent such as a hydrocarbon or a chlorinated hydrocarbon such as benzene, toluene, xylene, chlorobenzene, dichloromethane, chloroform or dichloroethane, an ether such as THF, dioxane, dibutyl ether, diisopropyl ether or DME, an amide such as DMF or NMP, or a mixture of solvents at temperatures of from about 20° C. to about 150° C., for example at temperatures of from about 50° C. to about 120° C. Prior to the reaction with the compound of the formula IX, an alkanesulfinic acid may also separately be treated with a base and converted into a salt.

The order of the steps in the preparation of the compounds of the formula I can also be changed, and the group -A-R³, for example, can be introduced at an earlier stage by reacting a compound of the formula VII in which R' is a leaving group, or by reacting a compound of the formula VII, which contains the group L¹ according to the above definition, which had been obtained from a compound of the formula VII by con verting the group R' into the group L¹, using a compound of the formula III and reacting the product obtained with a compound of the formula VIII to give the compound of the formula I. The above statements concerning the reaction of the compounds of the formulae II and III and the reaction of the compounds of the formulae VII and VIII apply correspondingly to corresponding reaction steps in such a synthesis of the compounds of the formula I.

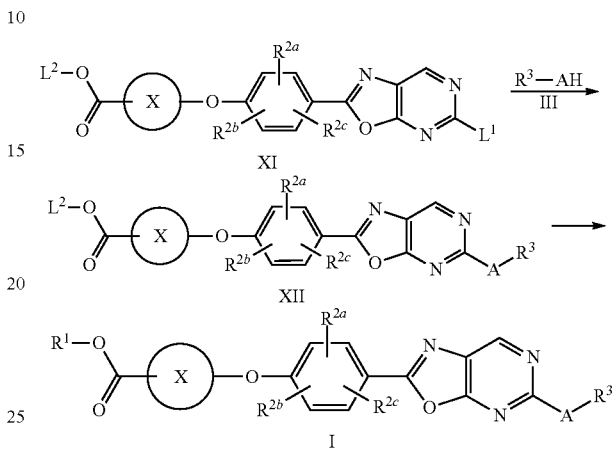

Accordingly, the order of the steps in the conclusion of the synthesis of compounds of the formula I can also be changed. For example, in the synthesis described above, R¹ may be present as leaving group L² in the compound XII, which leaving group is removed at the last synthesis step to liberate the group R¹. For example, L¹ is a benzyl group which is removed under suitable conditions, for example a hydrogenation. A summary of methods to remove protective groups can be found in the literature, for example in P. J. Kocienski, Protecting Groups (Thieme Verlag, 1994), or T. W. Greene and P. G. M. Wuts, Protective Groups in Organic Synthesis (John Wiley & Sons, 1999).

Further compounds of the formula I can be obtained from suitable compounds prepared according to the above-described processes by functionalization or modification of any functional groups present according to standard procedures, for example by esterification, amidation, hydrolysis, etherification, alkylation, acylation, sulfonylation, reduction, oxidation, conversion into salts, and others. For example, a hydroxyl group, which may be liberated from an ether group by ether cleavage, for example by means of boron tribromide, or from a protected hydroxyl group by deprotection, can be esterified to give a carboxylic acid ester or a sulfonic acid ester, or etherified. Etherifications of hydroxyl groups can favorably be performed by alkylation with the respective halogen compound, for example a bromide or iodide, in the presence of a base, for example an alkaline metal carbonate such as potassium carbonate or cesium carbonate, in an inert solvent, for example an amide like DMF or NMP or a ketone like acetone or butan-2-one, or with the respective alcohol under the conditions of the Mitsunobu reaction referred to above. A hydroxyl group can be converted into a halide by treatment with a halogenating agent. A halogen atom can be replaced with a variety of groups in a substitution reaction which may also be a transition metal-catalyzed reaction. A nitro group can be reduced to an amino group, for example by catalytic hydrogenation. An amino group can be modified under standard conditions for alkylation, for example by reac tion with a halogen compound or by reductive amination of a carbonyl compound, or for acylation or sulfonylation, for example by reaction with a reactive carboxylic acid derivative, like an acid chloride or anhydride or a sulfonic acid chloride, or with an activated carboxylic acid which may be obtained from the carboxylic acid by treatment with a coupling agent like N,N'-carbonyldiimidazole (CDI), a carbodiimide such as 1,3-dicyclohexylcarbodiimide (DCC) or 1-(3-dimethylaminopropyl)-3-ethylcarbodiimide hydrochloride (EDC), O-(7-azabenzotriazol-1-yl)-N,N,N',N'-tetramethyluronium hexafluorophosphate (HATU), O-(cyano(ethoxycarbonyl)methyleneamino)-N,N,N',N'-tetramethyluronium tetrafluoroborate (TOTU) or [(benzotriazol-1-yloxy)dimethylaminomethylene]dimethylammonium tetrafluoroborate (TBTU), for example. A carboxylic ester group can be hydrolyzed under acidic or basic conditions to give a carboxylic acid. A carboxylic acid group can be activated or converted into a reactive derivative as mentioned above and reacted with an alcohol or an amine or ammonia to give an ester or amide. A primary amide can be dehydrated to give a nitrile. A sulfur atom, for example in an alkyl-S group or in a heterocyclic ring, can be oxidized with a peroxide like hydrogen peroxide or a peracid to give a sulfoxide moiety $S(O)$ or a sulfone moiety $S(O)_2$. A carboxylic acid group, a carboxylic acid ester group and a ketone group can be reduced to an alcohol, for example by means of a complex hydride such as lithium aluminum hydride, lithium borohydride or sodium borohydride.

All reactions used in the above-described syntheses of the compounds of the formula I are per se well known to the skilled person and can be carried out under standard conditions according to, or analogously to, procedures described in the literature, for example in Houben-Weyl, Methoden der Organischen Chemie (Methods of Organic Chemistry), Thieme-Verlag, Stuttgart, or Organic Reactions, John Wiley & Sons, New York. If desired, the obtained compounds of the formula I, as well as any intermediate compounds, can be purified by customary purification procedures, for example by recrystallization or chromatography. As already mentioned, all starting compounds and intermediates employed in the above-described syntheses which contain an acidic or basic group can also be employed in the form of salts, and all intermediates and final target compounds can also be obtained in the form of salts. As likewise mentioned above, depending on the circumstances of the specific case, in order to avoid an unwanted course of a reaction or side reactions during the synthesis of a compound it can generally be necessary or advantageous to temporarily block functional groups by introducing protective groups and deprotect them again at a later stage of the synthesis, or to introduce functional groups in the form of precursor groups which later are converted into the desired functional groups. As examples of protective groups amino-protective groups may be mentioned which can be acyl groups or alkyloxycarbonyl groups, for example a tert-butyloxycarbonyl group (=Boc) which can be removed by treatment with trifluoroacetic acid (=TFA), a benzyloxycarbonyl group which can be removed by catalytic hydrogenation, or a fluoren-9-ylmethoxycarbonyl group which can be removed by treatment with piperidine, and protective groups of carboxylic acid groups which can be protected as ester groups, such as tert-butyl esters which can be deprotected by treatment with trifluoroacetic acid, or benzyl esters which can be deprotected by catalytic hydrogenation. As an example of a precursor group the nitro group, which can be converted into an amino group by reduction, for example by catalytic hydrogenation, may be mentioned. Such synthesis strategies, and protective groups and precursor groups which are suitable in a specific case, are known to the skilled person.

Another subject of the present invention are the novel starting compounds and intermediates occurring in the synthesis of the compounds of the formula I, including the compounds of the formulae II, III, IV, V, VI, VII, VIII, IX, XI and XII in which A, X, $R^1$, $R^{2a}$, $R^{2b}$, $R^{2c}$, $R^3$, R', $FG^1$, $FG^2$, $L^1$ and $L^2$ are defined as above, in any of their stereoisomeric forms or a mixture of stereoisomeric forms in any ratio, and their salts and solvates of such compounds or such salts, and their use as intermediates. The invention also includes all tautomeric forms of said intermediates and starting compounds. All explanations given above and embodiments specified above with respect to the compounds of the formula I also apply correspondingly to said intermediates and starting materials. Subject of the invention are in particular the novel specific starting compounds and intermediates disclosed herein. Independently of whether they are disclosed as a free compound and/or as a specific salt, they are a subject of the invention both in the form of the free compounds and in the form of their salts, and if a specific salt is disclosed, additionally in the form of this specific salt, and in the form of solvates of such compounds or such salts.

The compounds of the formula I, optionally in combination with other pharmacologically active compounds, can be administered to animals, preferably to mammals including humans, as pharmaceuticals by themselves, in mixtures with one another, or in the form of pharmaceutical compositions. The administration can be carried out orally, for example in the form of tablets, film-coated tablets, sugar-coated tablets, granules, hard and soft gelatin capsules, solutions including aqueous, alcoholic and oily solutions, juices, drops, syrups, emulsions or suspensions, rectally, for example in the form of suppositories, or parenterally, for example in the form of solutions for subcutaneous, intramuscular or intravenous injection or infusion, in particular aqueous solutions. The compounds of the formula I can additionally be used in modes of local drug delivery, for example in coated stents for preventing or reducing in-stent restenosis or by applying them locally by means of a catheter. The appropriate administration form depends, among others, on the disease to be treated and on its severity.

The compounds of the formula I can also be administered topically. Pharmaceutical compositions suitable for topical use on the skin are in the form of ointment, cream, lotion, paste, gel, hydrogel, spray, aerosol or oil. Carriers which can be used are petrolatum, lanolin, polyethylene glycols, alcohols and combinations of two or more of these substances. The active ingredient is generally present in a concentration of 0.0001 to 15% by weight of the composition, for example 0.0005 to 2%.

In one embodiment, the topical preparation is present as a gel.

In a further embodiment, the topical formulation is present as a hydrogel.

A hydrogel is understood as meaning a polymer which comprises, but is insoluble in, water, and whose molecules are linked chemically, for example by covalent or ionic bonds, or physically, for example by loop formation of the polymer chains, to form a three-dimensional network. Owing to incorporated hydrophilic polymer components, they swell in water with a considerable increase in volume, but without losing their material hold. A hydrogel consists, for example, of a hydrophilic solvent (for example water), a moisturizer (for example glycerol) and a gel former (for example croscarmellose-sodium).

The examples below show suitable gel preparations:

PREPARATION EXAMPLE 1

| | |
|---|---|
| Compound of example 1 | 0.0004% |
| Glycerol 85% | 10% |
| Methylparaben | 0.2% |
| Propylparaben | 0.03% |
| Croscarmellose-sodium | 4% |
| HCl/NaOH | qs (to adjust the pH to 7.5) |
| Water | ad 100% |

PREPARATION EXAMPLE 2

| | |
|---|---|
| Compound of example 1 | 0.04% |
| Glycerol 85% | 10% |
| Methylparaben | 0.2% |
| Propylparaben | 0.03% |
| Croscarmellose-sodium | 4% |
| HCl/NaOH | qs (to adjust the pH to 7.5) |
| Water | ad 100% |

PREPARATION EXAMPLE 3

| | |
|---|---|
| Compound of example 1 | 0.0004% |
| PEG400 | 10% |
| Methylparaben | 0.2% |
| Propylparaben | 0.03% |
| Croscarmellose-sodium | 4% |
| HCl/NaOH | qs (to adjust the pH to 7.5) |
| Water | ad 100% |

PREPARATION EXAMPLE 4

| | |
|---|---|
| Compound of example 1 | 0.04% |
| PEG400 | 10% |
| Methylparaben | 0.2% |
| Propylparaben | 0.03% |
| Croscarmellose-sodium | 4% |
| HCl/NaOH | qs (to adjust the pH to 7.5) |
| Water | ad 100% |

The hydrogels are preparations for dermal application The hydrogels can be applied to open wound regions. The hydrogels comprise the medicament in dissolved form, thus ensuring rapid skin and tissue penetration.

An aseptic preparation process ensures that no additional microbiological contaminations enter the wound as a result of the application of the medicament. In one embodiment, preservatives (methyl- and propylparaben) are additionally incorporated into the hydrogel to keep the pathogen load low.

In one embodiment, the hydrogel comprises the compounds of the formula I in concentrations of 0.04-0.0004% (m/m).

The aseptic hydrogel is stored in suitable sterile containers. In one embodiment, the hydrogel is stored in sterile containers made of polypropylene.

The amount of a compound of the formula I and/or its physiologically acceptable salts and/or solvates present in the pharmaceutical compositions normally ranges from about 0.2 to about 800 mg, for example from about 0.5 to about 500 mg, for example from about 1 to about 200 mg, per unit dose, but depending on the type of the pharmaceutical composition it may also be higher. The pharmaceutical compositions usually comprise from about 0.5 to about 90 percent by weight of the compound of the formula I and/or its physiologically acceptable salts and/or solvates. The production of the pharmaceutical compositions can be carried out in a manner known per se. To this end, one or more compounds of the formula I and/or their physiologically acceptable salts and/or solvates together with one or more solid or liquid pharmaceutical carrier substances, or vehicles, and/or additives, or auxiliary substances, and, if a combination medicament is desired, other pharmacologically active compounds having therapeutic or prophylactic action are brought into a suitable form for administration and dosage which can be used in human or veterinary medicine. As carrier substances and additives, suitable organic and inorganic substances can be used which do not react in an undesired manner with the compounds of the formula I or their physiologically acceptable salts or solvates. As examples of types of additives which can be contained in the pharmaceutical compositions and medicaments, lubricants, preservatives, thickeners, stabilizers, disintegrants, wetting agents, agents for achieving a depot effect, emulsifiers, salts, for example for influencing the osmotic pressure, buffer substances, colorants, flavorings and aromatic substances may be mentioned. Examples of carrier substances and additives are water, physiological sodium chloride solution, vegetable oils, waxes, alcohols such as ethanol, isopropanol, 1,2-propanediol, benzyl alcohols or glycerol, polyols, mannitol, polyethylene glycols, polypropylene glycols, glycerol triacetate, polyvinylpyrrolidone, gelatin, cellulose, carbohydrates such as lactose, glucose, saccharose or starch like corn starch, stearic acid and its salts such as magnesium stearate, talc, lanolin, petroleum jelly, or mixtures thereof, for example mixtures of water with one or more organic solvents such as mixtures of water with alcohols. The compounds of the formula I and their physiologically acceptable salts and solvates can also be lyophilized and the obtained lyophilisates used for the production of injectable compositions, for example.

The dosage of a compound of the formula I and/or a physiologically acceptable salt and/or solvate thereof to be administered depends on the specific case and, as is usual, has to be adapted by the physician according to the customary rules and procedures to the individual circumstances in order to achieve an optimum effect. It depends, for example, on the nature and the severity of the disorder to be treated, the sex, age, weight and individual responsiveness of the human or animal patient, on the efficacy and duration of action of the compound used, on whether the treatment is for the therapy of an acute or chronic disease or prophylactic, or on whether other active compounds are administered in addition to a compound of the formula I. In general, a daily dose from about 0.01 mg/kg to about 100 mg/kg, or from about 0.1 mg/kg to about 10 mg/kg, or from about 0.3 mg/kg to about 5 mg/kg (in each case mg per kg of bodyweight), for example, is appropriate for administration to an adult weighing 75 kg in order to obtain the desired results. The daily dose can be administered in a single dose or, in particular when larger amounts are administered, divided into several, for example two, three or four, individual doses. The administration can also be carried out continuously, for example by continuous infusion or injection. Depending on the individual behavior in a specific case, it may be necessary to deviate upward or downward from the indicated dosages.

The examples below illustrate the invention.

When example compounds containing a basic group were purified by preparative high pressure liquid chromatography (HPLC) on reversed phase (RP) column material and, as customary, the eluent was a gradient mixture of water and acetonitrile containing trifluoroacetic acid (TFA), they were in part obtained in the form of their acid addition salt with trifluoroacetic acid, depending on the details of the workup such as evaporation or lyophilization conditions. In the names of the example compounds and their structural formulae any such trifluoroacetic acid present is not specified.

The prepared compounds were in general characterized by spectroscopic data and chromatographic data, in particular mass spectra (MS) and HPLC retention times (Rt; in min) which were obtained by combined analytical HPLC/MS characterization (LC/MS), and/or nuclear magnetic resonance (NMR) spectra. In the NMR characterization, the chemical shift δ (in ppm), the number of hydrogen atoms and the multiplicity (s=singlet, d=doublet, dd=double doublet, t=triplet, dt=double triplet, q=quartet, m=multiplet; br=broad) of the signals are given. In the MS characterization, in general the mass number (m/z) of the peak of the molecular ion M, e.g. M⁺, or of a related ion such as the ion M+1, e.g. [M+1]⁺, i.e. the protonated molecular ion [M+H]⁺, which was formed depending on the ionization method used, is given. Generally, the ionization method was electrospray ionization (ESI). The LC/MS conditions used were as follows.

Method LC1
Column: HPLC BEH C18, 50×2.1 mm, 1.7 μm; flow rate: 0.9 ml/min; eluent A: water+0.1% formic acid; eluent B: acetonitrile+0.08% formic acid; gradient: from 95% A+5% B to 5% A+95% B in 1.1 min, then 5% A+95% B for 0.6 min; MS ionization method: ESI⁺

Method LC2 (FRA)
Column: Phenomenex, 4 μM, 10×2 mm, 1.7 μm; flow rate: 1.1 ml/min; eluent A: water+0.05% trifluoroacetic acid; eluent B: acetonitrile; gradient: from 93% A+7% B to 5% A+95% B in 1.2 min, then 5% A+95% B for 0.2 min; MS ionization method: ESI⁺

Method LC3
Column: HPLC BEH C18, 50×2.1 mm, 1.7 μm; flow rate: 0.9 ml/min; eluent A: water+0.05% formic acid; eluent B: acetonitrile+0.035% formic acid; gradient: from 98% A+2% B to 5% A+95% B in 2 min, then 5% A+95% B for 0.6 min; MS ionization method: ESI⁺

Method LC4
Column: XBridge C18, 50×4.6 mm, 2.5 μm; flow rate: 0.9 ml/min; eluent A: water+0.1% formic acid; eluent B: acetonitrile+0.1% formic acid; gradient: from 97% A+3% B to 40% A+60% B in 3.5 min, then from 40% A+60% B to 2% A+98% B in 0.5 min, then 2% A+98% B for 1 min; MS ionization method: ESI⁺

EXAMPLE 1

3-{4-[5-(3-Chlorophenoxy)oxazolo[5,4-d]pyrimidin-2-yl]-2,6-dimethylphenoxy}cyclobutanecarboxylic acid

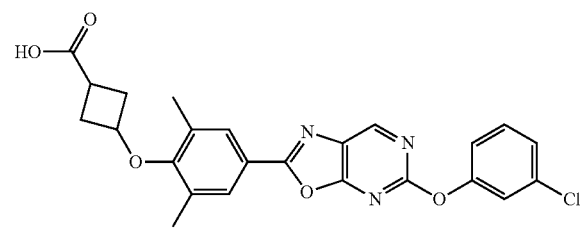 [SMILES: Cc1cc(-c2nc3cnc(Oc4cccc(Cl)c4)nc3o2)cc(C)c1OC1CC(C(=O)O)C1]

(a) N-(2,4-Dichloropyrimidin-5-yl)-4-methoxy-3,5-dimethylbenzamide

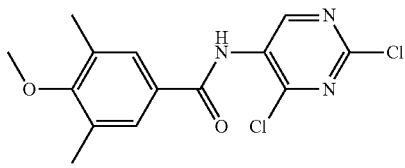 [SMILES: COc1c(C)cc(C(=O)Nc2cnc(Cl)nc2Cl)cc1C]

3.2 g of 5-amino-2,4-dichloropyrimidine in 50 ml ethyl acetate were added to a mixture of 25 ml of saturated aqueous sodium bicarbonate solution and 25 ml of water. At room temperature, a solution of 4.9 g of 3,5-dimethyl-4-methoxybenzoyl chloride was added over a period of 15 min. The mixture was stirred intensively for 4 h. The layers were then separated, after which the aqueous layer was extracted twice with ethyl acetate. After drying over sodium sulfate and filtration, the solvent was removed under reduced pressure, giving 7.54 g of crude product. The crude product was triturated with 25 ml of isopropanol. Filtration and washing with 10 ml of isopropanol gave 2.74 g of the title compound in the form of a white solid.

LC/MS (Method LC2): Rt=1.00 min; m/z=326.0; 328.0 [M+H]⁺ (dichloro pattern)

(b) 5-Chloro-2-(4-methoxy-3,5-dimethylphenyl)oxazolo[5,4-d]pyrimidine

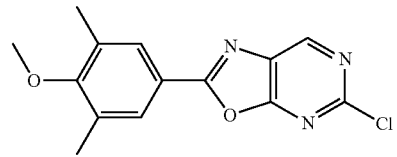 [SMILES: COc1c(C)cc(-c2nc3cnc(Cl)nc3o2)cc1C]

A solution of 2.74 g of N-(2,4-dichloropyrimidin-5-yl)-4-methoxy-3,5-dimethylbenzamide and 3.2 ml of N,N-diisopropylethylamine in 17 ml of acetonitrile was split into two charges, each of which was heated in a microwave reactor at 160° C. for 1 h. The charges were recombined and the precipitate was then filtered off, which gave 600 mg of the title compound in the form of a dark, but relatively pure, solid (600 mg). After evaporation of the solvents from the mother liquor under reduced pressure, the residue was subjected to silica gel chromatography (heptane/ethyl acetate gradient), which gave a further 600 mg of the title compound in the form of a pale-yellow solid.

LC/MS (Method LC2): Rt=1.08 min; m/z=290.0 [M+H]⁺

(c) 4-(5-Chlorooxazolo[5,4-d]pyrimidin-2-yl)-2,6-dimethylphenol

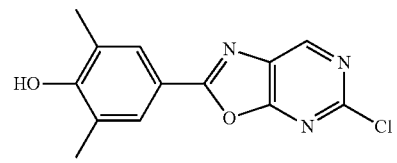 [SMILES: Cc1cc(-c2nc3cnc(Cl)nc3o2)cc(C)c1O]

A solution of 1.2 g of 5-chloro-2-(4-methoxy-3,5-dimethylphenyl)oxazolo[5,4-d]pyrimidine in 42 ml of dichloromethane was cooled to 0° C., and 10 ml of a 1 M solution of boron tribromide in dichloromethane were added over a period of 10 min. The mixture was stirred at 0° C. for 1 h, and a further 3 ml of a 1 M solution of boron tribromide in dichloromethane were then added. After another hour of stirring, 20 ml of saturated aqueous sodium bicarbonate solution were added slowly. The precipitate was filtered off and washed with water, which gave 1 g of the title compound.

LC/MS (Method LC2): Rt=0.93 min; m/z=276.0 [M+H]+

(d) Benzyl 3-[4-(5-chlorooxazolo[5,4-d]pyrimidin-2-yl)-2,6-dimethylphenoxy]cyclobutanecarboxylate

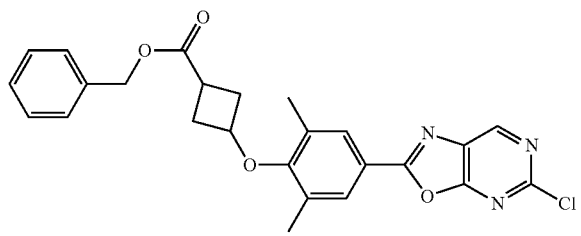 [SMILES: Cc1cc(-c2nc3cnc(Cl)nc3o2)cc(C)c1OC1CC(C(=O)OCc2ccccc2)C1]

At 0° C., 1.14 g of triphenylphosphine and 0.69 ml of diethyl azodicarboxylate were initially charged in 30 ml of tetrahydrofuran, and the mixture was stirred for 15 min. 1.00 g of 4-(5-chlorooxazolo[5,4-d]pyrimidin-2-yl)-2,6-dimethylphenol, 0.61 ml of triethylamine and 0.90 g of benzyl 3-hydroxycyclobutanecarboxylate were then added, and the reaction was stirred under argon, initially at room temperature for 6 h. Another 1.14 g of triphenylphosphine and 0.69 ml of diethyl azodicarboxylate were then added, and the reaction was stirred for 12 h. After another addition of 1.14 g of triphenylphosphine and 0.69 ml of diethyl azodicarboxylate and 2 further hours of reaction time at room temperature, the reaction was concentrated and the resulting residue was purified by flash chromatography (silica gel, heptane/ethyl acetate). This gave 1.45 g (86%) of the title compound.

LC/MS (Method LC1): Rt=1.46 min; m/z=464.1 [M+H]+

(e) Benzyl 3-[4-(5-methanesulfonyloxazolo[5,4-d]pyrimidin-2-yl)-2,6-dimethylphenoxy]cyclobutanecarboxylate

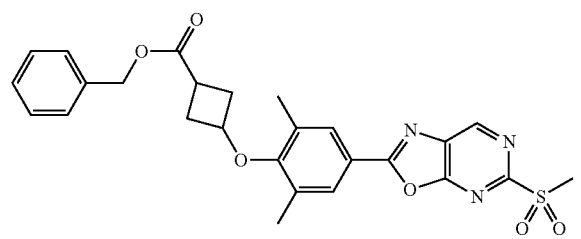 [SMILES: Cc1cc(-c2nc3cnc(S(C)(=O)=O)nc3o2)cc(C)c1OC1CC(C(=O)OCc2ccccc2)C1]

A solution of 200 mg of benzyl 3-[4-(5-chlorooxazolo[5,4-d]pyrimidin-2-yl)-2,6-dimethylphenoxy]cyclobutanecarboxylate and 48 mg of sodium methylsulfinate in 4 ml of N,N-dimethylformamide was heated in a microwave reactor at 100° C. for 60 min. At room temperature, the mixture was filtered and then washed with DMF. The filtrate was concentrated and the resulting residue was purified by preparative HPLC. This gave 71 mg (32%) of the title compound.

LC/MS (Method LC1): Rt=1.36 min; m/z=508.1 [M+H]+

(f) Benzyl 3-{4-[5-(3-chlorophenoxy)oxazolo[5,4-d]pyrimidin-2-yl]-2,6-dimethylphenoxy}cyclobutanecarboxylate

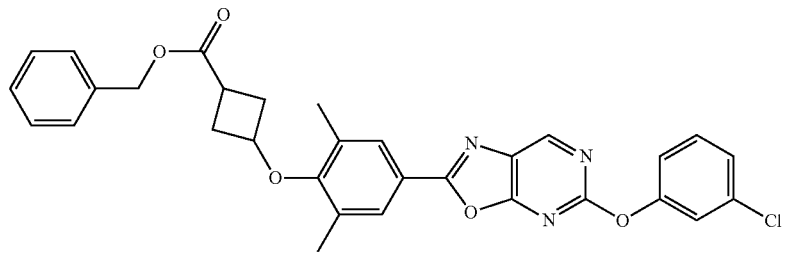 [SMILES: Cc1cc(-c2nc3cnc(Oc4cccc(Cl)c4)nc3o2)cc(C)c1OC1CC(C(=O)OCc2ccccc2)C1]

48 mg of potassium carbonate and 20 mg of 3-chlorophenol were added to a solution of 70 mg of benzyl 3-[4-(5-methanesulfonyloxazolo[5,4-d]pyrimidin-2-yl)-2,6-dimethylphenoxy]cyclobutanecarboxylate in 5 ml of N,N-dimethylformamide. The reaction mixture was stirred at room temperature for 1.5 h and at 60° C. for a further 4 h. For work-up, 10% strength aqueous citric acid solution was added, and the reaction was extracted with dichloromethane. The combined organic phases were concentrated and dried under reduced pressure. This gave 77 mg (100%) of the title compound, which was reacted further without any purification.

LC/MS (Method LC1): Rt=1.51 min; m/z=566.1 [M+H]+

(g) 3-{4-[5-(3-Chlorophenoxy)oxazolo[5,4-d]pyrimidin-2-yl]-2,6-dimethylphenoxy}cyclobutanecarboxylic acid

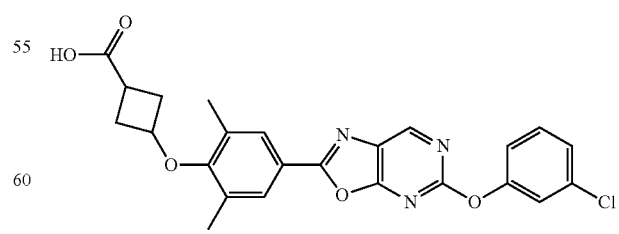

77 mg of benzyl 3-{4-[5-(3-chlorophenoxy)oxazolo[5,4-d]pyrimidin-2-yl]-2,6-dimethylphenoxy}cyclobutanecarboxylate were dissolved in 4.4 ml of ethyl acetate, 2.5 mg of palladium on carbon (5%)

were added and the mixture was hydrogenated at 3 bar and room temperature. After 5 h, the catalyst was filtered off. The filtrate was concentrated, and purification by preparative HPLC gave 20 mg (32%) of the title compound.

LC/MS (Method LC1): Rt=1.36 min; m/z=466.1 [M+H]⁺

EXAMPLE 2

3-{4-[5-(2-Fluorophenoxy)oxazolo[5,4-d]pyrimidin-2-yl]-2,6-dimethylphenoxy}cyclobutanecarboxylic acid

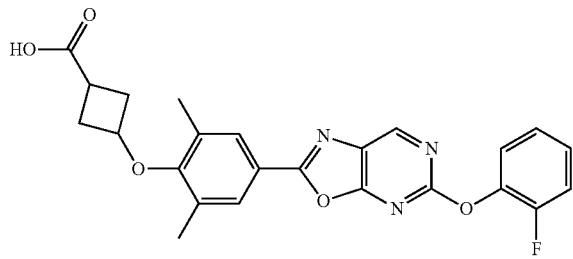 [SMILES: Cc1cc(-c2nc3cnc(Oc4ccccc4F)nc3o2)cc(C)c1OC1CC(C(=O)O)C1]

(a) 4-[5-(2-Fluorophenoxy)oxazolo[5,4-d]pyrimidin-2-yl]-2,6-dimethylphenol

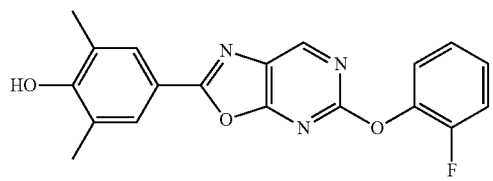 [SMILES: Cc1cc(-c2nc3cnc(Oc4ccccc4F)nc3o2)cc(C)c1O]

Under argon, 0.48 g of sodium hydride (60% in mineral oil) is added a little at a time to a solution of 1.12 ml of 2-fluorophenol in 40 ml of dry N,N-dimethylacetamide. After 30 min at room temperature, a suspension of 2.78 g of 4-(5-chlorooxazolo[5,4-d]pyrimidin-2-yl)-2,6-dimethylphenol (see Ex. 1 (c)) in 60 ml of dry N,N-dimethylacetamide is added, and the reaction is stirred at 60° C. for 1.5 h and at 80° C. for 5.5 h. Another 1.12 ml of 2-fluorophenol in 40 ml of dry N,N-dimethylacetamide were then reacted under argon with 0.48 g of sodium hydride (60% in mineral oil), and this mixture was added to the reaction at room temperature. After a further 9 h at 80° C., the reaction was cooled to room temperature and neutralized with 10% strength aqueous citric acid solution. The precipitated solid was filtered off with suction, washed with water and dried under reduced pressure at 45° C. This gave 3.37 g (96%) of the title compound, which was reacted without any further purification.

LC/MS (Method LC2): Rt=1.03 min; m/z=352.1 [M+H]⁺

(b) Benzyl 3-{4-[5-(2-fluorophenoxy)oxazolo[5,4-d]pyrimidin-2-yl]-2,6-dimethylphenoxy}cyclobutanecarboxylate

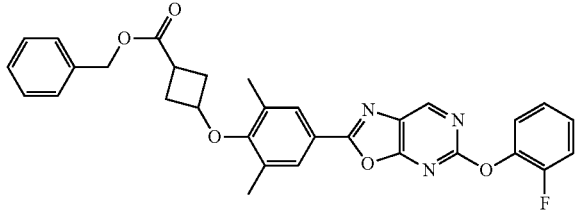 [SMILES: Cc1cc(-c2nc3cnc(Oc4ccccc4F)nc3o2)cc(C)c1OC1CC(C(=O)OCc2ccccc2)C1]

At 0° C., 179 mg of triphenylphosphine and 107 μl of diethyl azodicarboxylate were initially charged in 4.5 ml of tetrahydrofuran, and the mixture was stirred for 15 min. 200 mg of 4-[5-(2-fluorophenoxy)oxazolo[5,4-d]pyrimidin-2-yl]-2,6-dimethylphenol, 95 μl of triethylamine and 141 mg of benzyl 3-hydroxycyclobutanecarboxylate were then added to the reaction, and the reaction was stirred under argon, initially at room temperature for 3 h. Another 179 mg of triphenylphosphine and 107 μl of diethyl azodicarboxylate were then added, and the reaction was stirred for 12 h. For work-up, the reaction was concentrated and the resulting residue was purified by flash chromatography (silica gel, heptane/ethyl acetate). This gave 216 mg (70%) of the title compound.

LC/MS (Method LC2): Rt=1.32 min; m/z=540.1 [M+H]⁺

(c) 3-{4-[5-(2-Fluorophenoxy)oxazolo[5,4-d]pyrimidin-2-yl]-2,6-dimethylphenoxy}cyclobutanecarboxylic acid

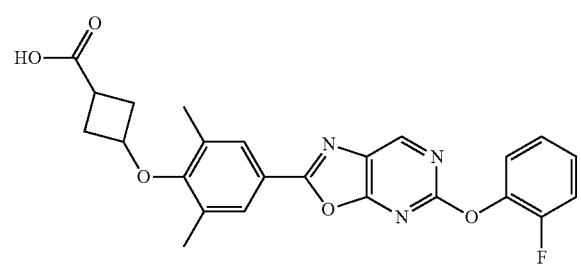 [SMILES: Cc1cc(-c2nc3cnc(Oc4ccccc4F)nc3o2)cc(C)c1OC1CC(C(=O)O)C1]

Analogously to example 1 (g), 216 mg of benzyl 3-{4-[5-(2-fluorophenoxy)oxazolo[5,4-d]pyrimidin-2-yl]-2,6-dimethylphenoxy}cyclobutanecarboxylate were reacted in a catalytic hydrogenation to give 83 mg (46%) of the title compound.

LC/MS (Method LC1): Rt=1.33 min; m/z=450.1 [M+H]⁺

Further examples prepared analogously to Example 1 are listed in Table 2 below

TABLE 2

II

| Example | X | R3 | LC/MS Method | m/z [M+H]+ | Rt [min] |
|---|---|---|---|---|---|
| 3 | 1,3-cyclobutyldiyl | 2,4-difluorophenyl | LC3 | 468.23 | 2.05 |
| 4 | 1,3-cyclobutyldiyl | 2-fluoro-3-trifluoromethylphenyl | LC3 | 518.24 | 2.12 |
| 5 | 1,3-cyclobutyldiyl | 2-chlorophenyl | LC4 | 466.24 | 4.82 |
| 6 | 1,3-cyclobutyldiyl | 3,5-difluorophenyl | LC3 | 468.24 | 2.08 |
| 7 | 1,3-cyclobutyldiyl | 3-chloro-4-fluorophenyl | LC4 | 484.26 | 4.89 |
| 8 | 1,3-cyclobutyldiyl | 2,3-difluorophenyl | LC3 | 468.25 | 2.06 |
| 9 | 1,3-cyclobutyldiyl | 3-chloro-2-fluorophenyl | LC4 | 484.26 | 4.9 |
| 10 | 1,3-cyclobutyldiyl | 4-fluoro-3-methylphenyl | LC3 | 464.26 | 2.08 |
| 11 | 1,3-cyclobutyldiyl | 3-fluorophenyl | LC3 | 450.24 | 2.04 |

TABLE 2-continued

Structure II:
HO-C(=O)-[X]-O-(2,6-dimethylphenyl)-oxazolo[5,4-d]pyrimidine-O-R³

| Example | X | R3 | LC/MS Method | m/z [M+H]+ | Rt [min] |
|---|---|---|---|---|---|
| 12 | 1,3-cyclobutyldiyl | 4-chloro-2-fluorophenyl | LC4 | 484.26 | 4.91 |
| 13 | 1,3-cyclobutyldiyl | 2-methylphenyl | LC3 | 446.25 | 2.04 |
| 14 | 1,4-cyclohexyldiyl | 2-fluorophenyl | LC3 | 477.26 | 2.04 |
| 15 | 1,3-cyclobutyldiyl | cyclohexylmethyl | LC3 | 452.32 | 2.11 |
| 16 | 1,3-cyclobutyldiyl | isobutyl | LC3 | 412.28 | 1.97 |
| 17 | 1,3-cyclobutyldiyl | 3,3,3-trifluoropropyl | LC4 | 452.19 | 4.7 |
| 18 | 1,3-cyclobutyldiyl | cyclopropylethyl | LC3 | 424.28 | 1.97 |

Determination of the Pharmacological Activity

A) GTP-γ-S Assay Using Human Edg-1 Receptors

In order to determine the Edg-1 receptor activation by the compounds of the invention, a GTP-γ-S ((GTP-γ-S=guanosine 5'-[thio]triphosphate) assay for G-protein coupled receptor binding based on the scintillation proximity assay principle was used, employing a cell membrane preparation from a CHO Flp-In cell line which constitutively overexpresses the human Edg-1 receptor.

(a) Cell Line Generation

The Flp-In™ expression system (Invitrogen/Life Technologies™ cat. no. K6010-01) allows the generation of stable mammalian cell lines into which the gene of interest has been integrated through homologous recombination at a specific genomic location called Flp Recombination Target (FRT) site by means of a Flp recombinase encoded by the pOG44 expression plasmid. The integration of the pcDNA5/FRT expression construct into the Flp-In host cell line genome results in the transcription of the gene of interest. The stably transfected cells become hygromycin-resistant.

One day prior to transfection, 200 000 Flp-In-CHO cells were seeded in Ham F-12 medium (Invitrogen/Life Technologies™, cat. no. 31765) supplemented with 10% fetal calf serum (FCS; Perbio Science, cat. no. SH30068.03) in a 6-well plate and incubated at 37° C./5% $CO_2$ overnight. Using the FuGENE® 6 transfection reagent (Roche, cat. no. 11988387001), cells were cotransfected with the Flp recombinase expression plasmid pOG44 and a modified plasmid additionally containing the edg-1 gene (accession no. NM_001400) and termed as pcDNA5-FRT-TO_nFLAG_DEST-EDG-1 with a 9:1 ratio. To obtain the modified pcDNA5-FRT-TO_nFLAG_DEST plasmid, the plasmid pcDNA5/FRT/TO (Invitrogen/Life Technologies™, cat. no. V6520-20) was adapted to the Gateway® (Invitrogen/Life Technologies™) cloning system by inserting a Gateway cassette containing attR recombination sites flanking a ccdB gene and a chloramphenicol-resistance gene (Gateway conversion system, Invitrogen/Life Technologies™, cat. no. 11828-029). In addition a FLAG tag epitope was added before the 5' att recombination site to allow recombinant expression of N-terminally FLAG-tagged proteins.

For the transfection of one well, 1.08 μg of pOG44 and 0.12 μg of pcDNA5-FRT-TO_nFLAG_DEST-EDG-1 were mixed to 100 μl of serum-free Ham F-12 medium containing 6 μl of FuGENE® 6 transfection reagent. After 20 min of incubation, the transfection reagent/DNA complex was distributed dropwise on the cells. The cells were incubated for 24 h at 37° C. Then the cells from 3 wells were transferred to a T75 flask (Greiner Cellstar®, cat. no. 658175) containing Ham F-12 medium supplemented with 10% of FCS but without antibiotic and were incubated another 24 h. 48 h after transfection, the medium was replaced by selection medium (Ham F-12 supplemented with 10% of FCS and 300 μg/ml of hygromycin B (Invitrogen/Life Technologies™, cat. no. 10687-010)). The medium was exchanged every 2 to 3 days until a resistant population of cells had grown. Cells were several times split and seeded into a new flask so that the cells did not reach more than 25% of confluency. After 2 weeks of selection, the cells were transferred into T175 flasks (Greiner Cellstar®, cat. no. 660175) and cultivated for batch production. Cells were harvested from the culture flasks by short treatment (2 to 5 min) with Accutase (PAA, cat. no. L11-007), resuspended in selection medium (see above) and centrifuged at 200×g for 5 min. Cells were resuspended in a mixture of 90% of FCS and 10% of dimethyl sulfoxide and stored frozen in liquid nitrogen.

(b) Membrane Preparation

A membrane preparation was obtained by standard methods from the afore-described CHO Flp-In cell line constitutively overexpressing the human Edg-1 receptor. To this end, the cryopreserved cells were taken in culture and grown until confluency in T150 cell culture flasks (Becton Dickinson, cat. no. 35 5001). Cell culture was stopped by washing with calcium-free phosphate-buffered saline (PBS; Gibco, cat. no. 14190), and cells were harvested with a rubber-policeman in 4° C. cold and calcium-free PBS supplemented with a protease inhibitor cocktail (complete protease inhibitor; Roche, cat. no. 1873580; 1 tablet per 50 ml) and subsequently centrifuged at 4° C. for 15 min at 1100×g (Heraeus Minifuge T). For cell lysis, the pellet was resuspended in a 4° C. cold hypotonic buffer consisting of 5 mM HEPES (Gibco 1M, cat. no. 15630), 1 mM EDTA (disodium salt; Sigma-Aldrich 0.5 M, cat. No. E-7889) supplemented with protease inhibitor cocktail (as above) in which cells were stored for another 15 min on ice. After lysis, cells were centrifuged at 4° C. for 10 min at 400×g (Heraeus Minifuge T). The pellet was disrupted in a Dounce homogenizer, diluted with the supernatant of the previous centrifugation and subsequently centrifuged at 4° C. for 10 min at 500×g (Heraeus Minifuge T) in order to separate nuclei and still intact cells from the membranes mainly present in the supernatant. The supernatant was then diluted in hypotonic buffer and centrifuged (Beckmann, Avanti J251) at approximately 18600×g for 2 hours at 4° C. After centrifugation, the membrane pellet was resuspended in a buffer consisting of 20 mM HEPES; 150 mM NaCl (Sigma-Aldrich, cat. no. S-3014), 1 mM EDTA (as above) supplemented with protease inhibitor cocktail (as above). The membrane preparation was aliquoted and stored at −80° C. Protein concentration of the membrane preparation was determined in a sample by means of a commercial protein assay (Bio-Rad, DC Protein Assay, cat. nos. 500-0113, 500-0114, 500-0115).

(c) GTP-γ-S-Assay

The EDG-1 membrane preparation obtained in (b) was initially used in a commercial scintillation proximity assay kit (Amersham/GE Healthcare, cat. no. RPNQ0210) to quantify the receptor activation. Here, the ligand-induced binding of $^{35}$S-radiolabeled GTP-γ-S to the receptor-containing membrane causes the emission of light in the scintillation beads attached to the membrane preparation, which allows quantification of the in vitro activity of the Edg-1-agonistic compound. The assay was performed on a 96-well plate substantially according to the manufacturer's instructions. Later on, scintillation beads and $^{35}$S-radiolabeled GTP-γ-S were also obtained from Perkin Elmer (cat. no. RPNQ0001) and Biotrend Chemikalien GmbH (cat. no. SCS-302). Before start of the experiments, scintillation beads were suspended in a reconstitution buffer consisting of Tris-HCl (pH 7.4) (Sigma-Aldrich cat. no. T-2194, 1M trizma HCl) and subsequently, on ice, adjusted to pH 7.4 with assay buffer (consisting of 20 mM HEPES, 100 mM NaCl, 1 mM EDTA (as above), 1 mM dithiothreitol (DTT, Sigma-Aldrich cat. no. D-9163)) and diluted to a final bead concentration of 30 mg/ml.

The wells in question were charged with 20 µl of the specified assay buffer, 10 µl of a 100 µM guanosine diphosphate (GDP) solution, and 10 µl of a solution of the test compound in assay buffer/dimethyl sulfoxide resulting in a final concentration of the test compound of 10 µM. For the positive controls, 10 µl of a solution of sphingosine-1-phosphate (S1P; Sigma-Aldrich, cat. no. S-9666), resulting in a final S1P concentration of 10 µM, and for the negative controls 10 µl of assay buffer (without ligand), were added into the wells in question instead of the solution of the test compound. All wells contained equivalent amounts of dimethyl sulfoxide. Then 10 µl of a [$^{35}$S]GTP-γ-S solution (4 nM) and the Edg-1 membrane preparation obtained in (b) (15 µg membrane protein in 100 µl of assay buffer) were added to each well. After incubation of the plates at room temperature for 5 min, 50 µl of the scintillation bead suspension described (30 mg/ml) were added. After a further incubation period of 45 min at room temperature, the plates were centrifuged for 10 min at 500×g.

Quantification of [$^{35}$S]GTP-γ-S binding and thus receptor activation was measured by means of a scintillation counter for beta radiation (Wallac, MicroBeta) over 1 min. Values were background-corrected by subtraction of the respective negative control. All measurements were made in triplicate. The receptor activation by the test compound is expressed in percent of the respective positive control (10 µM S1P; regarded as 100% activation). In Table 3 activations observed with example compounds at 10 µM are listed.

TABLE 3

Edg-1 receptor activation by example compounds at 10 µM in percent of the activation by 10 µM S1P

| Example | % activation |
|---------|--------------|
| 1  | 116 |
| 2  | 83  |
| 3  | 116 |
| 4  | 105 |
| 5  | 108 |
| 6  | 133 |
| 7  | 107 |
| 8  | 105 |
| 9  | 114 |
| 10 | 115 |
| 11 | 113 |
| 12 | 108 |
| 13 | 112 |
| 14 | 74  |
| 15 | 67  |
| 16 | 55  |
| 17 | 98  |
| 18 | 88  |

It can be seen from the measurement data that, in view of their pharmacological activity, the compounds are highly suitable for wound healing and in particular for treating wound healing disorders of patients with diabetes.

The invention claimed is:
1. A compound of the formula I, in any of its stereoisomeric forms, or a mixture of stereoisomeric forms in any ratio, or a physiologically acceptable salt thereof, or a physiologically acceptable solvate of such a compound or such a salt,

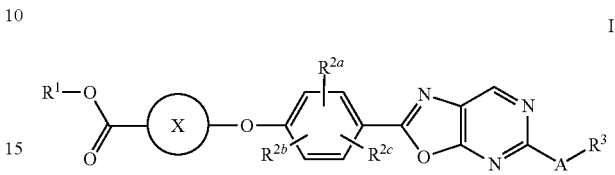

wherein
A is selected from the group consisting of NH, O and S;
X is $(C_3-C_7)$-cycloalkanediyl which is optionally substituted by one or more identical or different substituents selected from the group consisting of $(C_1-C_4)$-alkyl, fluorine and hydroxyl;
$R^1$ is selected from the group consisting of hydrogen, $(C_1-C_4)$-alkyl and $(C_3-C_7)$-cycloalkyl-$C_zH_{2z}$—, where z is selected from the group consisting of 0, 1 and 2;
$R^{2a}$, $R^{2b}$ and $R^{2c}$ are selected independently of one another from the group consisting of hydrogen, halogen, hydroxyl, $(C_1-C_4)$-alkyl-, $(C_3-C_5)$-cycloalkyl-$C_zH_{2z}$—, $(C_1-C_4)$-alkyloxy, $(C_1-C_4)$-alkyl-S(O)$_m$—, amino, nitro, cyano, hydroxycarbonyl, $(C_1-C_4)$-alkyloxycarbonyl, aminocarbonyl and aminosulfonyl, where z is selected from the group consisting of 0, 1 and 2;
$R^3$ is selected from the group consisting of $(C_1-C_6)$-alkyl, $(C_2-C_6)$-alkenyl, $(C_2-C_6)$-alkynyl, $(C_3-C_7)$-cycloalkyl-$C_uH_{2u}$— and Het-$C_vH_{2v}$—, where u and v are selected from the group consisting of 1 and 2, or $R^3$ is a radical of a saturated or unsaturated 3-membered to 10-membered monocyclic or
bicyclic ring which contains 0, 1, 2, 3 or 4 identical or different ring heteroatoms selected from the group consisting of N, O and S, where one or two of the ring nitrogen atoms may carry a hydrogen atom or a $(C_1-C_4)$-alkyl substituent and one or two of the ring sulfur atoms may carry one or two oxo groups and where the radical of a ring is optionally substituted at one or more ring carbon atoms by identical or different substituents $R^{31}$;
$R^{31}$ is selected from the group consisting of halogen, $(C_1-C_4)$-alkyl, $(C_3-C_7)$-cycloalkyl, hydroxyl, $(C_1-C_4)$-alkyloxy, oxo, $(C_1-C_4)$-alkyl-S(O)$_m$—, amino, $(C_1-C_4)$-alkylamino, di(($C_1-C_4$)-alkyl)amino, $(C_1-C_4)$-alkylcarbonylamino, $(C_1-C_4)$-alkylsulfonylamino, nitro, cyano, $(C_1-C_4)$-alkylcarbonyl, aminosulfonyl, $(C_1-C_4)$-alkylaminosulfonyl and di(($C_1-C_4$)-alkyl)aminosulfonyl;
Het is a radical of a saturated 4-membered to 7-membered monocyclic heterocycle which contains 1 or 2 identical or different ring heteroatoms selected from the group consisting of N, O and S and which is attached via a ring carbon atom, where the radical of a heterocycle is optionally substituted by one or more identical or different substituents selected from the group consisting of fluorine and $(C_1-C_4)$-alkyl;
m is selected from the group consisting of 0, 1 and 2;
where all cycloalkyl and cycloalkanediyl groups independently of one another and independently of other substituents are optionally substituted by one or more identical or different substituents selected from the group consisting of fluorine and $(C_1-C_4)$-alkyl;

where all alkyl, alkanediyl, $C_uH_{2u}$, $C_vH_{2v}$, $C_zH_{2z}$, alkenyl, alkenediyl, alkynyl and alkynediyl groups independently of one another and independently of other substituents may optionally be substituted by one or more fluorine substituents.

2. The compound of the formula I, in any of its stereoisomeric forms, or a mixture of stereoisomeric forms in any ratio, or a physiologically acceptable salt thereof, or a physiologically acceptable solvate of such a compound or such a salt as claimed in claim 1, wherein A is O or S;

X is $(C_3-C_7)$-cycloalkanediyl;

$R^{2a}$, $R^{2b}$ and $R^{2c}$ independently of one another are hydrogen, halogen, hydroxyl, $(C_1-C_4)$-alkyl, $(C_1-C_4)$-alkyloxy, $(C_1-C_4)$-alkyl-S(O)$_m$—, amino, nitro or cyano;

$R^1$ is hydrogen or $(C_1-C_4)$-alkyl;

$R^3$ is $(C_1-C_6)$-alkyl, $(C_3-C_7)$-cycloalkyl-$C_uH_{2u}$— or Het-$C_vH_{2v}$—, where u and v are selected from the group consisting of 1 and 2, or $R^3$ is a radical of a saturated or unsaturated 3-membered to 10-membered monocyclic or bicyclic ring which contains 0, 1 or 2 identical or different ring heteroatoms selected from the group consisting of N, O and S, where one or two of the ring nitrogen atoms may carry a hydrogen atom or a $(C_1-C_4)$-alkyl substituent and one of the ring sulfur atoms may carry one or two oxo groups and where the radical of a ring is optionally substituted at one or more ring carbon atoms by identical or different substituents $R^{31}$;

$R^{31}$ is halogen, $(C_1-C_4)$-alkyl, $(C_3-C_7)$-cycloalkyl, hydroxyl, $(C_1-C_4)$-alkyloxy, oxo, $(C_1-C_4)$-alkyl-S(O)$_m$—, amino, $(C_1-C_4)$-alkylamino, di($(C_1-C_4)$-alkyl)amino, $(C_1-C_4)$-alkylcarbonylamino, $(C_1-C_4)$-alkylsulfonylamino, nitro, cyano, $(C_1-C_4)$-alkylcarbonyl, aminosulfonyl, $(C_1-C_4)$-alkylaminosulfonyl or di($(C_1-C_4)$-alkyl)aminosulfonyl;

Het is a radical of a saturated 4-membered to 6-membered monocyclic heterocycle which contains 1 ring heteroatom selected from the group consisting of N, O and S and which is attached via a ring carbon atom, where the radical of a heterocycle is optionally substituted by one or more identical or different substituents selected from the group consisting of fluorine and $(C_1-C_4)$-alkyl;

m is 0, 1 or 2;

where all cycloalkyl and cycloalkanediyl groups independently of one another and independently of other substituents are optionally substituted by one or more identical or different substituents selected from the group consisting of fluorine and $(C_1-C_4)$-alkyl;

where all alkyl, alkanediyl, $C_uH_{2u}$, $C_vH_{2v}$, $C_zH_{2z}$, alkenyl, alkenediyl, alkynyl and alkynediyl groups independently of one another and independently of other substituents may optionally be substituted by one or more fluorine substituents.

3. The compound of the formula I, in any of its stereoisomeric forms, or a mixture of stereoisomeric forms in any ratio, or a physiologically acceptable salt thereof, or a physiologically acceptable solvate of such a compound or such a salt as claimed in claim 1, wherein A is O;

X is $(C_3-C_7)$-cycloalkanediyl;

$R^1$ is hydrogen;

$R^{2a}$, $R^{2b}$ and $R^{2c}$ independently of one another are hydrogen, halogen, hydroxyl, $(C_1-C_4)$-alkyl or $(C_1-C_4)$-alkyloxy;

$R^3$ is $(C_1-C_6)$-alkyl, $(C_3-C_7)$-cycloalkyl-$C_uH_{2u}$— or Het-$C_vH_{2v}$—, where u and v are selected from the group consisting of 0 and 1, or $R^3$ is a radical of a saturated or unsaturated 3-membered to 7-membered monocyclic or bicyclic ring which contains 0, 1 or 2 identical or different ring heteroatoms selected from the group consisting of N, O and S, where one or two of the ring nitrogen atoms may carry a hydrogen atom or a $(C_1-C_4)$-alkyl substituent and one of the ring sulfur atoms may carry one or two oxo groups and where the radical of a ring is optionally substituted at one or more ring carbon atoms by identical or different substituents $R^{31}$;

$R^{31}$ is halogen, $(C_1-C_4)$-alkyl, $(C_3-C_7)$-cycloalkyl, hydroxyl or $(C_1-C_4)$-alkyloxy;

Het is a radical of a saturated 4-membered to 6-membered monocyclic heterocycle which contains 1 ring heteroatom selected from the group consisting of O and S and which is attached via a ring carbon atom, where the radical of a heterocycle is optionally substituted by one or more identical or different substituents selected from the group consisting of fluorine and $(C_1-C_4)$-alkyl;

where all alkyl, cycloalkanediyl, $C_uH_{2u}$ and $C_vH_{2v}$ groups independently of one another and independently of other substituents are optionally substituted by one or more fluorine substituents.

4. The compound of the formula I, in any of its stereoisomeric forms, or a mixture of stereoisomeric forms in any ratio, or a physiologically acceptable salt thereof, or a physiologically acceptable solvate of such a compound or such a salt as claimed in claim 1 wherein A is O;

X is $(C_3-C_7)$-cycloalkanediyl;

$R^1$ is hydrogen;

$R^{2a}$, $R^{2b}$ and $R^{2c}$ independently of one another are hydrogen, halogen, hydroxyl, $(C_1-C_4)$-alkyl or $(C_1-C_4)$-alkyloxy;

$R^3$ is a radical of a saturated or unsaturated, 3-membered to 7-membered, monocyclic ring which contains 0 or 1 ring heteroatom selected from the group consisting of N, O and S, where a ring nitrogen atom may carry a hydrogen atom or a $(C_1-C_4)$-alkyl substituent and a ring sulfur atom may carry one or two oxo groups and where the radical of a ring is optionally substituted at one or more ring carbon atoms by identical or different substituents $R^{31}$;

$R^{31}$ is halogen, $(C_1-C_4)$-alkyl, $(C_3-C_7)$-cycloalkyl, hydroxyl or $(C_1-C_4)$-alkyloxy;

where all cycloalkyl groups independently of one another and independently of other substituents are optionally substituted by one or more identical or different substituents selected from the group consisting of fluorine and $(C_1-C_4)$-alkyl;

where all alkyl and cycloalkanediyl groups independently of one another and independently of other substituents are optionally substituted by one or more fluorine substituents.

5. The compound of the formula I, in any of its stereoisomeric forms, or a mixture of stereoisomeric forms in any ratio, or a physiologically acceptable salt thereof, or a physiologically acceptable solvate of such a compound or such a salt as claimed in claim 1, wherein A is O;

X is $(C_3-C_7)$-cycloalkanediyl;

$R^1$ is hydrogen;

$R^{2c}$ is hydrogen;

$R^{2a}$ and $R^{2b}$ independently of one another are $(C_1-C_4)$-alkyl;

R³ is phenyl, where the phenyl ring is optionally substituted at one or more ring carbon atoms by identical or different substituents R³¹;

R³¹ is halogen, $(C_1-C_4)$-alkyl, $(C_3-C_7)$-cycloalkyl, hydroxyl or $(C_1-C_4)$-alkyloxy;

where all cycloalkyl groups independently of one another and independently of other substituents are optionally substituted by one or more identical or different substituents selected from the group consisting of fluorine and $(C_1-C_4)$-alkyl;

where all alkyl and cycloalkanediyl groups independently of one another and independently of other substituents are optionally substituted by one or more fluorine substituents.

6. A pharmaceutical composition, comprising at least one compound of the
formula I as claimed in claim 1 or a physiologically acceptable salt thereof,
or a physiologically acceptable solvate of such a compound or such a salt, and a pharmaceutically acceptable carrier.

7. The pharmaceutical composition as claimed in claim 6, wherein the pharmaceutical composition is a hydrogel preparation.

8. A method of treating wound healing disorders in a patient in need thereof comprising administering to said patient a therapeutically effective amount of the pharmaceutical composition of claim 6.

9. A method of wound healing in a patient in need thereof comprising administering to said patient a therapeutically effective amount of the pharmaceutical composition of claim 6.

10. A method of wound healing in diabetics in a patient in need thereof comprising administering to said patient a therapeutically effective amount of the pharmaceutical composition of claim 6.

11. A method of treating diabetic foot syndrome in a patient in need thereof comprising administering to said patient a therapeutically effective amount of the pharmaceutical composition of claim 6.

* * * * *